(12) United States Patent
Lin et al.

(10) Patent No.: US 9,046,650 B2
(45) Date of Patent: Jun. 2, 2015

(54) METHODS AND APPARATUS FOR MID-INFRARED SENSING

(71) Applicants: Pao Tai Lin, Brighton, MA (US); Yan Cai, Stoughton, MA (US); Anuradha Murthy Agarwal, Weston, MA (US); Lionel C. Kimerling, Concord, MA (US)

(72) Inventors: Pao Tai Lin, Brighton, MA (US); Yan Cai, Stoughton, MA (US); Anuradha Murthy Agarwal, Weston, MA (US); Lionel C. Kimerling, Concord, MA (US)

(73) Assignee: The Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/076,655

(22) Filed: Nov. 11, 2013

(65) Prior Publication Data
US 2014/0264030 A1    Sep. 18, 2014

Related U.S. Application Data

(60) Provisional application No. 61/777,834, filed on Mar. 12, 2013.

(51) Int. Cl.
*G01J 5/20*    (2006.01)
*G02B 6/136*    (2006.01)
(Continued)

(52) U.S. Cl.
CPC .............. *G02B 6/136* (2013.01); *G02B 6/122* (2013.01); *G01N 21/35* (2013.01)

(58) Field of Classification Search
CPC ...................................................... G01N 21/35
USPC ........................................ 250/338.1–338.5
See application file for complete search history.

(56) References Cited

U.S. PATENT DOCUMENTS 5,677,196 A * 10/1997 Herron et al. ................. 436/518
5,917,967 A *  6/1999 Dubey et al. .................... 385/14
(Continued)

FOREIGN PATENT DOCUMENTS

JP    2007-183644 A    7/2007
WO    WO 00/07411 A1    2/2000
(Continued)

OTHER PUBLICATIONS

Cheng et al., "Single polarization transmission in pedestal-supported silicon waveguides," 2011, Optics Letters, vol. 36, No. 10, pp. 1797-1799.*

(Continued)

*Primary Examiner* — Kiho Kim
(74) *Attorney, Agent, or Firm* — Cooley LLP

(57) ABSTRACT

A chip-scale, air-clad semiconductor pedestal waveguide can be used as a mid-infrared (mid-IR) sensor capable of in situ monitoring of organic solvents and other analytes. The sensor uses evanescent coupling from a silicon or germanium waveguide, which is highly transparent in the mid-IR portion of the electromagnetic spectrum, to probe the absorption spectrum of fluid surrounding the waveguide. Launching a mid-IR beam into the waveguide exposed to a particular analyte causes attenuation of the evanescent wave's spectral components due to absorption by carbon, oxygen, hydrogen, and/or nitrogen bonds in the surrounding fluid. Detecting these changes at the waveguide's output provides an indication of the type and concentration of one or more compounds in the surrounding fluid. If desired, the sensor may be integrated onto a silicon substrate with a mid-IR light source and a mid-IR detector to form a chip-based spectrometer.

32 Claims, 24 Drawing Sheets

(51) Int. Cl.
*G01N 21/35* (2014.01)
*G02B 6/122* (2006.01)

(56) References Cited

U.S. PATENT DOCUMENTS

| | | |
|---|---|---|
| 7,336,859 B2 | 2/2008 | Sanders |
| 7,382,032 B2 | 6/2008 | Kolodzey et al. |
| 7,480,434 B2 | 1/2009 | Hochberg et al. |
| 7,519,253 B2 | 4/2009 | Islam |
| 7,778,499 B2 | 8/2010 | Janz et al. |
| 7,920,267 B2 * | 4/2011 | Cho et al. ............. 356/445 |
| 7,949,210 B2 | 5/2011 | Durfee et al. |
| 2005/0077513 A1 | 4/2005 | Fan et al. |
| 2006/0180762 A1 | 8/2006 | Kolodzey et al. |
| 2007/0297462 A1 | 12/2007 | Jalali et al. |
| 2008/0008418 A1 | 1/2008 | Smith et al. |
| 2009/0136190 A1 | 5/2009 | Berini et al. |
| 2009/0206242 A1 | 8/2009 | Mizaikoff et al. |
| 2012/0014837 A1 * | 1/2012 | Fehr et al. ............. 422/82.11 |
| 2012/0226118 A1 | 9/2012 | Delbeke et al. |

FOREIGN PATENT DOCUMENTS

| | | |
|---|---|---|
| WO | WO 2011/140544 A2 | 11/2011 |
| WO | WO 2012/109733 A1 | 8/2012 |

OTHER PUBLICATIONS

International Search Report and Written Opinion, issued Feb. 25, 2014, in corresponding International Patent Application No. PCT/US2013/069687.

\* cited by examiner

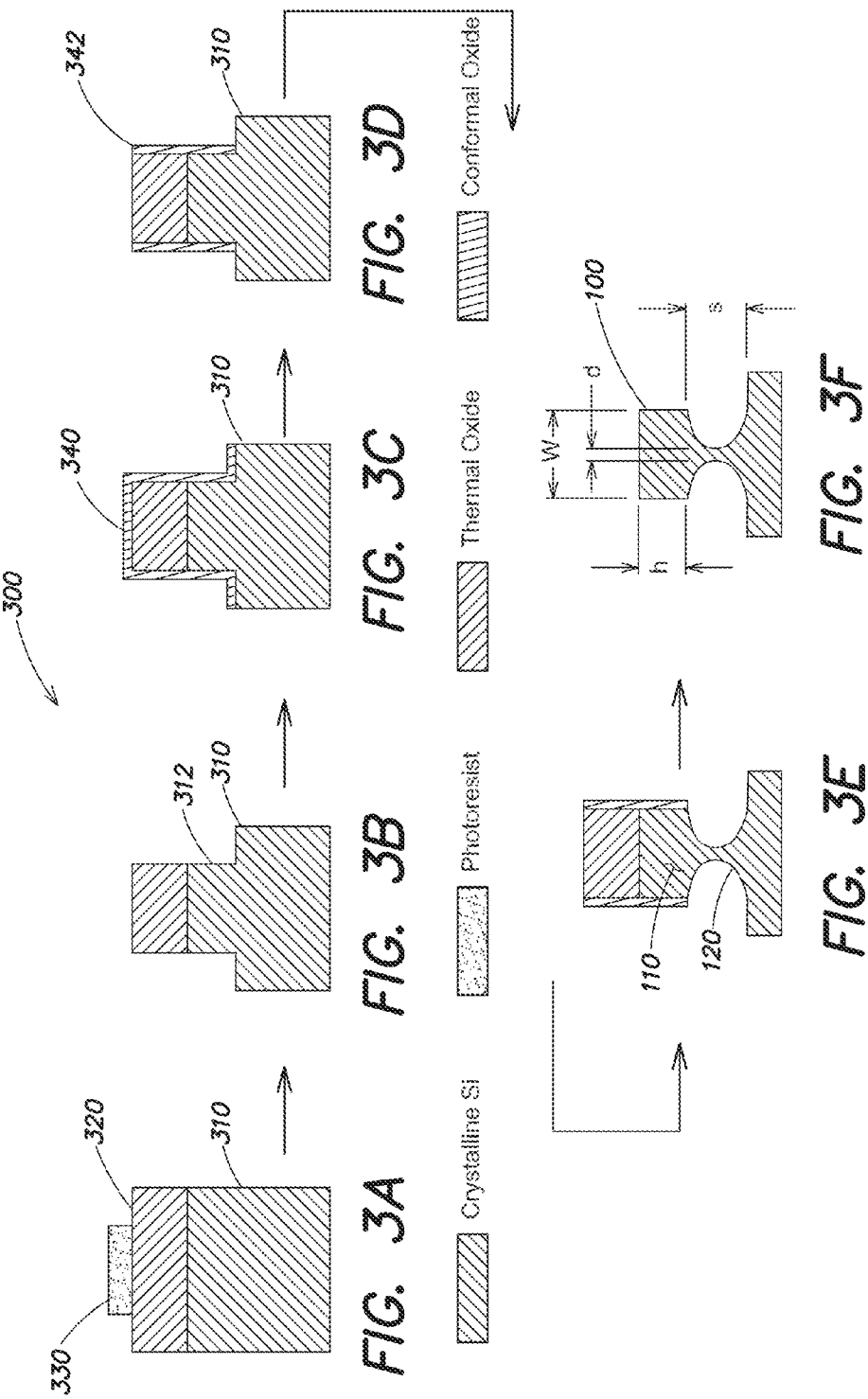

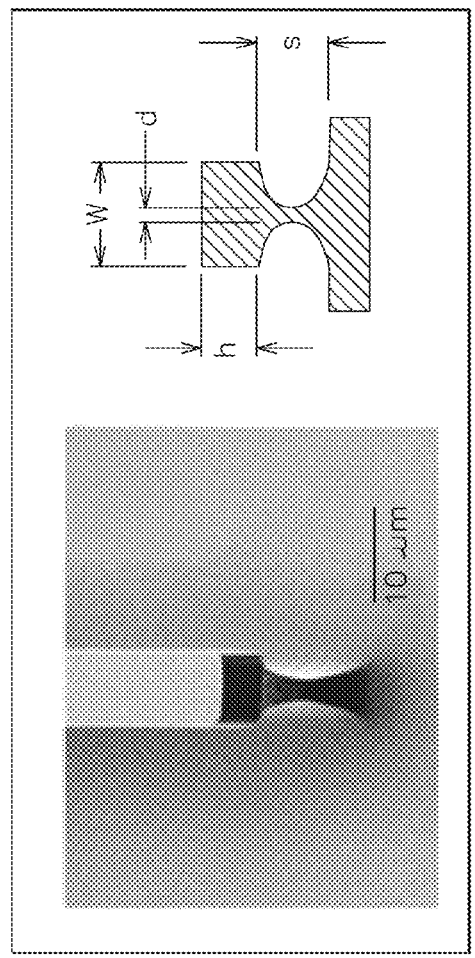
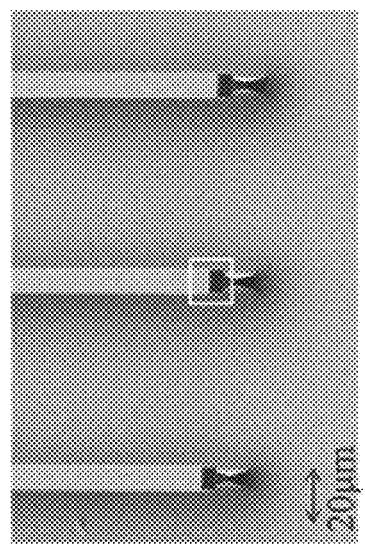
FIG. 4B
FIG. 4A

US 9,046,650 B2

METHODS AND APPARATUS FOR MID-INFRARED SENSING

CROSS-REFERENCE TO RELATED PATENT APPLICATION

This application claims priority, under 35 U.S.C. §119(e), from U.S. Provisional Application 61/777,384, filed Mar. 12, 2013, entitled "Chip-Scale Broadband Mid-Infrared Chemical Sensors Using Silicon Waveguides," which application is hereby incorporated herein by reference in its entirety.

GOVERNMENT SUPPORT

This invention was made with government support under Contract No. DE-NA000421 from the Department of Energy. The government has certain rights in this invention.

BACKGROUND

Chemical sensor arrays using integrated photonics have attracted significant attention because of their potential for large area environmental monitoring and high throughput screening for biomedical discovery. Advanced technologies using absorbance, surface plasmon resonance (SPR), and fluorescence detection have been developed to realize chip-scale optical sensors. For instance, chemical sensors using micro-ring resonators with ppm-level detectivity have been demonstrated. SPR sensors using a perfect absorber or highly-doped semiconductors are utilized for multispectral infrared (IR) spectroscopy and gas identification.

Unfortunately, chip-scale mid-IR sensors have yet to be realized in silicon-integrated photonics. Silicon-integrated photonics are based mainly on conventional silicon-on-insulator (SOI) technology, in which a thin layer of silicon dioxide serves as an undercladding between the top crystalline silicon waveguide and the bottom crystalline silicon substrate to prevent light leakage through the substrate. Though SOI is mature and suitable for near infrared photonic circuits, it cannot be easily adopted for planar mid-infrared (mid-IR; e.g., $\lambda=3$ μm to 8 μm) devices since silicon dioxide becomes optically lossy at wavelengths greater than about 3.6 μm. Hence, conventional SOI devices are generally unsuitable for detecting absorption in the mid-IR portion of the electromagnetic spectrum.

Replacing the silicon dioxide layer with sapphire to create a silicon-on-sapphire (SOS) increases the transparency range beyond 3.6 μm, but may preclude chemical detection of double-bond functional groups, such as C═O, C═N, and C═C, with vibrational absorption between $\lambda=5$ μm and $\lambda=8$ μm, due to absorption by sapphire above $\lambda=5$ μm. Another platform using silicon on porous silicon was proposed for mid-IR devices, in which the waveguide cladding is a porous silicon layer created by high-energy proton beam irradiation and electrochemical etching. Though low-index silicon is obtained as the undercladding, the damage and scattering loss caused by high-energy proton beam irradiation has not yet been investigated.

SUMMARY

Embodiments of the present invention include devices and methods for sensing at least one molecule with a mid-infrared beam. In one example, a mid-infrared sensing device includes a silicon substrate, a silicon pedestal extending from the silicon substrate, and a semiconductor waveguide (e.g., a silicon or germanium waveguide) disposed on the silicon pedestal above the silicon substrate. In operation, the semiconductor waveguide guides the mid-infrared beam, which has at least one spectral component in a range of about 1.5 μm to about 12.0 μm. While the mid-infrared beam propagates through the semiconductor waveguide, the semiconductor waveguide's outer surface receives at least one molecule so as to cause absorption of the at least one spectral component by the at least one molecule. For instance, a fluid containing the molecule may be disposed on the semiconductor waveguide's outer surface. This absorption reduces the spectral component's intensity. A detector at the semiconductor waveguide's output may sense the intensity of the spectral component at one end of the semiconductor waveguide (e.g., the detector may include a spectrometer that senses the spectrum of the detected intensity).

In certain examples, the semiconductor waveguide, which may be made of silicon or germanium, confines only a first portion of the mid-infrared beam. Depending upon the embodiment, the semiconductor waveguide can have a width of about 1 μm to about 30 μm and a height of about 0.4 μm to about 50 μm. And the silicon pedestal that supports that semiconductor waveguide may have a minimum width of about 0.5 μm to about 2.5 μm and a height of about 1.0 μm to about 20 μm.

Examples of the sensor may also include a mid-infrared light source, such as a tunable laser, that is optically coupled to the semiconductor waveguide. In operation, the light source generates the mid-infrared beam and launches or couples it into one end of the semiconductor waveguide. In some cases, the light source and the detector may be disposed or formed on the silicon substrate as well.

The mid-infrared beam may be narrowband or broadband (e.g., with a bandwidth of about 1.0 μm to about 12.0 μm) depending on the application. If the mid-infrared light source is tunable, then the wavelength of the spectral component may be tuned as a function of time, e.g., so as to sweep across a particular spectral band. Detecting a change in the detected intensity of the spectral component as a function of time yields a representation of the molecule's absorption spectrum, which can be used to identify the molecule (and/or its presence).

Embodiments of the present technology also include methods of making a silicon waveguide on a silicon pedestal extending from a silicon substrate. An exemplary method includes forming a silicon ridge on the silicon substrate, then disposing a conformal layer of silicon dioxide on the silicon ridge so as to form a coated silicon ridge adjacent to an exposed portion of the silicon substrate. Etching the exposed portion of the silicon substrate yields a silicon pedestal that extends from the silicon substrate and supports the coated silicon ridge. Removing the conformal layer of silicon dioxide from the coated silicon ridge yields the silicon waveguide on the silicon pedestal.

The silicon ridge can be formed by depositing a silicon dioxide layer on the silicon substrate; patterning the silicon dioxide layer (e.g., via reactive ion etching or wet anisotropic etching) so as to form a silicon dioxide ridge on the silicon substrate; and etching the silicon substrate adjacent to the silicon dioxide ridge so as to form the silicon ridge beneath the silicon dioxide ridge. The silicon ridge's width can be about 1 μm to about 30 μm and its height can be about 1 μm to about 30 μm.

The conformal layer of silicon dioxide can be disposed on the silicon ridge by depositing a silicon dioxide layer on the silicon ridge and the silicon substrate. Once the silicon dioxide layer has been deposited, it can be anisotropically etched (e.g., via reactive ion etching or wet anisotropic etching) so as to form the exposed portion of the silicon substrate.

The exposed portion of the silicon substrate can be etched by exposure to $SF_6$. In some case, the exposed portion may etched to a depth of about 1 μm to about 20 μm so as to form the silicon pedestal with a height of about 1 μm to about 20 μm. The exposed portion of the silicon substrate may also be etched to form the silicon pedestal with a width of about 0.5 μm to about 2.5 μm.

Embodiments of the present technology also include methods of making a germanium waveguide on a silicon pedestal extending from a silicon substrate. An exemplary method comprises forming a germanium waveguide on the silicon substrate and anisotropically etching at least a portion of the silicon substrate so as to create a silicon pedestal that extends from the silicon substrate and supports the germanium waveguide. In certain examples, the germanium waveguide is formed by: forming an oxide layer on the silicon substrate; selectively etching the oxide layer to form a trench that extends to the silicon substrate; depositing germanium in the trench; and removing the oxide layer to form the germanium waveguide. In other examples, the germanium waveguide is formed by forming a germanium layer on the silicon substrate and selectively etching the germanium layer to form the germanium waveguide.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 3A-3F illustrate a process for fabricating silicon pedestal waveguides and splitters.

FIG. 4A is a scanning electron microscope (SEM) image of an array of fabricated air-clad silicon pedestal waveguides suitable for mid-IR sensing (the box indicates the view shown in FIG. 4B).

FIG. 4B is an SEM image of a fabricated silicon pedestal waveguide with a waveguide width w=8 μm, waveguide height h=5 μm, pedestal height s=14 μm, and pedestal width d=2 μm.

DETAILED DESCRIPTION

Figure 1A:
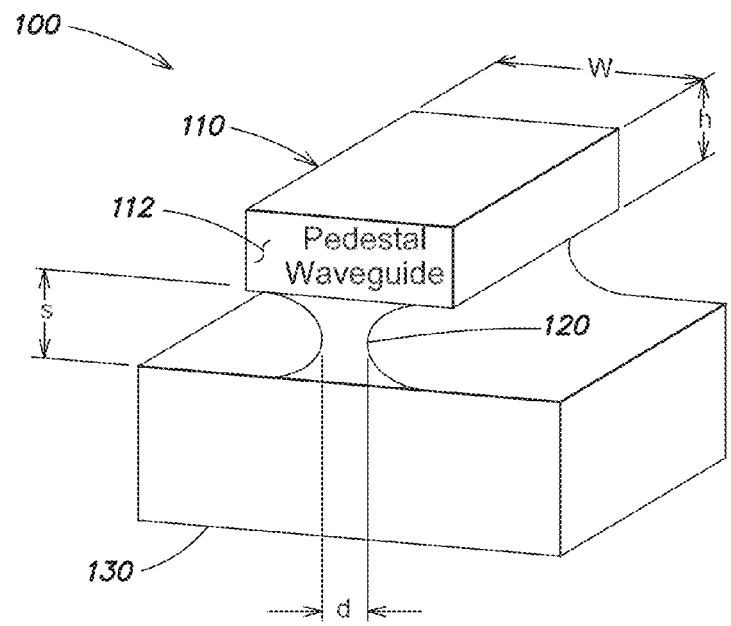
FIG. 1A is a perspective diagram of an exemplary air-clad, silicon pedestal waveguide suitable for mid-infrared (mid-IR) sensing with a waveguide width w, a waveguide height h, a pedestal height s, and a pedestal width d.

Embodiments of the present technology include air-clad semiconductor straight waveguides, bent waveguides, and splitter waveguides. Each of these waveguides utilizes a pedestal structure for broadband mid-infrared (mid-IR) devices and is compatible with complementary metal-oxide-semiconductor (CMOS) processes and hence amenable to large-scale manufacturing. Experimental results, including scanning electron microscope (SEM) images, confirm that exemplary devices retain their structural integrity during fabrication processing. Broadband mid-IR transmission characterization of exemplary devices shows a sharp fundamental waveguide mode, low mid-IR optical loss (e.g., 2.7 dB/cm), and, for certain waveguide splitters, a 50/50 power splitting ratio. These characteristics make exemplary air-clad semiconductor waveguides suitable for integrated mid-IR microphotonics, including mid-IR sensing applications.

For instance, an exemplary air-clad silicon or germanium pedestal waveguide can be used in mid-IR integrated photonics for spectroscopic sensing at wavelengths between 1.5 μm and 12.0 μm (e.g., between 1.5 μm and 8.0 μm, between 3.0 μm and 6.5 μm, between 5.0 μm and 12.0 μm, and so on). In one example, the device may include an air-clad silicon waveguide that is transparent up to about λ=6.5 μm, which is a wavelength regime that overlaps with many characteristic absorption peaks of organic/inorganic molecules. In another example, the device may include an air-clad germanium waveguide that is transparent up to about λ=12.0 μm, which is a wavelength regime that overlaps with vibrational absorption peaks associated with certain double-bond functional groups (e.g., C=O, C=N and C=C). Because these structures does not require silicon dioxide, they do not have the limitations associated with Silicon-On-Insulator (SOI) waveguide structures, which exhibit significant optical loss due to absorption in silicon dioxide ($SiO_2$) under-cladding layers above about λ=3.6 μm.

Air-clad semiconductor pedestal waveguides also offer advantages over Silicon-On-Sapphire (SOS) waveguides, including simpler (and less expensive) fabrication. Moreover, the cladding layer in an SOS waveguide weakens the interaction between the evanescent optical wave and the surrounding chemicals, consequently decreasing the SOS device's sensitivity. While chalcogenide glass (ChG) waveguide materials have a wider IR transparency, air-clad crystalline silicon is chemically and mechanically more robust because it is a single crystal (as opposed to a glass). In addition, the mature fabrication technology of very-large-scale integration (VLSI) makes silicon advantageous in sensor applications, enabling the fabrication of a wider range of sensor structures. These characteristics enable a mid-IR air-clad semiconductor pedestal waveguide sensor to perform (a) broadband mid-IR scanning, (b) real-time trace chemical detection, (c) concentration monitoring, and (d) identification of organic compounds.

If desired, one or more mid-IR air-clad semiconductor pedestal waveguide sensors can be integrated with one or more light sources and one or more photodetectors to form a mid-IR spectrometer-on-a-chip. The robust air-clad pedestal semiconductor sensor(s) can be tailored to perform chemical analyte detection using characteristic mid-IR absorption spectra to simultaneously perform qualitative (compound recognition) and quantitative (target concentration) analyses. Specifically, mid-IR spectra can "fingerprint" molecular structures within functional groups present in the chemical analytes, enabling label-free detection. These lab-on-a-chip broadband Mid-IR sensors can be used in many applications, including but not limited to remote real-time sensing of trace toxins and detection of contaminants.

Experimental testing of an exemplary silicon pedestal waveguide shows the advantages of silicon pedestal waveguides over surface plasmon resonance (SPR) devices for mid-IR sensing. Although SPR devices may have high sensitivity, the enhanced near-field surface plasmon polaritons arise in a narrow bandwidth where a resonance is observed. Conversely, a mid-IR sensor is a broadband sensor that can operate over a wide spectral range since no resonant state is required. In addition, a mid-IR sensor's sensitivity can be selected based on the desired application, with longer waveguides for greater sensitivity and shorter waveguides for lower sensitivity. Also, there are limited choices of either metallic or dielectric media for an SPR sensor suitable for use between λ=2 μm to λ=12 μm. Another challenge is that SPR requires a highly smooth dielectric/metal interface in order to avoid polariton scattering loss. But unlike SPR technology, a pedestal silicon or germanium waveguide can be built on a single mid-IR transparent material (silicon) that reduces or eliminates any complexity in device design and materials selection and provides very low propagation loss.

Semiconductor pedestal waveguides also provide advantages over optical sensors that use ultraviolet, visible, or near-infrared light to measure chemical concentration by sensing a shift of a resonant cavity's resonance frequency. Typically, these optical sensors use a frequency-swept or narrow linewidth source to probe a change in the cavity's refractive index caused by a change in the chemical concentration. Conversely, measuring the absorption of an evanescent wave, as in the sensors presented here, does not require a source with such a narrow linewidth or as great a frequency agility.

A mid-IR waveguide also provides various advantages over micro-resonators and reflectance filters, including a broader sensing spectrum. Even though micro-resonators can detect a very low concentration of analyte, their sensitivity depends on the accuracy of the sub-micron gap between a micro-ring and a waveguide. But a given gap-width is applicable only over a certain spectral range. For instance, a micro-ring resonator designed for $\lambda=2.4$-$2.6$ µm will not work properly at a longer wavelength, such as $\lambda=3.4$-$3.6$ µm, because the optimized coupling gap width shifts with the wavelengths. Unlike a resonator or filter, an exemplary waveguide sensor can measure changes in optical absorption over the entire transparency window of silicon (e.g., up to $\lambda=7$ µm) or germanium (e.g., up to $\lambda=12$ µm). Furthermore, waveguide sensor fabrication does not require the high-resolution (but low-speed) patterning techniques used for high Q-factor micro-ring resonators.

Although the sensors described below are made of silicon and germanium, one of skill in the art would readily understand that the sensor' and its components could each comprise any other suitable semiconductor material, including but not limited to pure semiconductor material, binary semiconductor materials (e.g., III-V compounds such as gallium arsenide), certain ternary compounds, and certain organic semiconductor materials.

Silicon Pedestal Waveguide Sensors

Figure 1B:
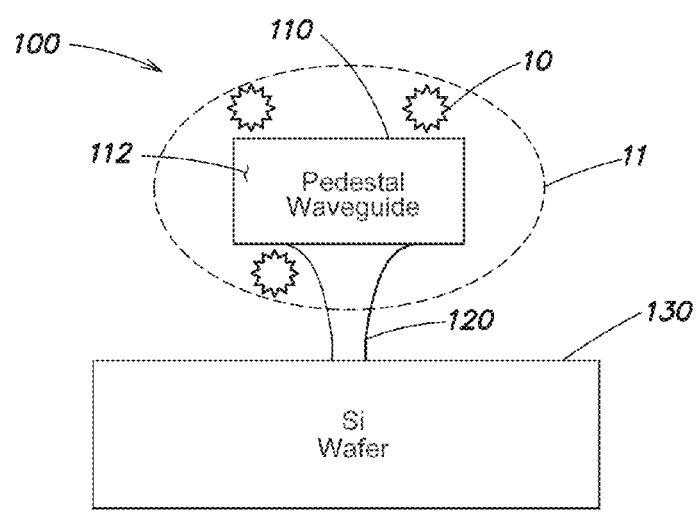
FIG. 1B is a diagram of the silicon pedestal waveguide of FIG. 1A used to sense organic molecules with an evanescent wave.

FIGS. 1A and 1B illustrate a silicon pedestal waveguide 100 suitable for sensing changes in concentration via evanescent absorption at wavelength(s) between about 3 µm and about 8 µm. The silicon pedestal waveguide 100 includes a silicon substrate (wafer) 130, a silicon pedestal 120 extending from the silicon substrate 130, and a silicon waveguide 110 supported above the silicon substrate 130 by the silicon pedestal 120. The silicon waveguide 110 also defines an exterior surface 112, through which an evanescent wave 11 associated with the supported waveguide mode(s) interacts with one or more organic molecules 10 or other analytes.

As readily understood by those of skill in the art, the waveguide's shape and dimensions may be selected to support propagation of one or modes of a mid-IR electromagnetic wave. For example, the waveguide 110 shown in FIGS. 1A and 1B has a rectangular cross-section with a width w and a height h. Depending on the embodiment, the waveguide width w may be about 1 µm to about 30 µm (e.g., 2.5 µm, 5.0 µm, 7.5 µm, 10.0 µm, 12.5 µm, 15.0 µm, 17.5 µm, 20.0 µm, 22.5 µm, 25.0 µm, or 27.5 µm) and the waveguide height h may be about 1 µm to about 30 µm (e.g., 2.5 µm, 5.0 µm, 7.5 µm, 10.0 µm, 12.5 µm, 15.0 µm, 17.5 µm, 20.0 µm, 22.5 µm, 25.0 µm, or 27.5 µm). Other embodiments may have different cross-sectional shapes, including but not limited to circles, triangles, squares, pentagons, hexagon, octagons, etc.

In some cases, the silicon waveguide's shape and dimensions may be chosen to support propagation of only a single mode (e.g., the $TEM_{00}$ mode) of a beam with a wavelength of about 2 µm to about 8 µm. In other cases, the silicon waveguide's shape and dimensions may be chosen to support propagation of multiple modes at mid-IR wavelengths. If desired, the silicon waveguide 110 may include stress members and/or have a shape or composition selected to preserve the polarization state of the mid-IR beam propagating through the silicon waveguide 110. In other words, the silicon waveguide 110 may be a polarization-maintaining waveguide as readily understood by those of skill in the art.

Depending on the embodiment, the waveguide's shape and dimensions may also be chosen to support an evanescent wave (tail) that extends laterally out of the waveguide 110. As understood by those of skill in the art, an evanescent wave is a near-field wave whose intensity decays exponentially decay as a function of the distance from the boundary at which the evanescent wave is formed—in this case, the waveguide's outer surface 112. In operation, at least a portion of the evanescent wave may be absorbed by one or more molecules (e.g., organic molecules 10) within a length about equal to the evanescent wave's decay constant. For instance, the molecule(s) may absorb one or more of the evanescent wave's spectral components, leading to a spectrally selective reduction in intensity of the wave propagating through the waveguide 110. Detecting this spectrally selective reduction in intensity—e.g., by measuring the absorption spectrum—at the waveguide's output yields an indication of the type and concentration of molecules in the fluid surrounding the waveguide 110.

As shown in FIGS. 1A and 1B, the waveguide's outer surface 112 may be configured to receive or support at least one molecule (e.g., organic molecule 10) in the fluid surrounding the pedestal waveguide sensor 100. For instance, the outer surface 112 may be textured, patterned, and/or coated to promote adhesion of the molecules to the outer surface 112. In other cases, the outer surface 112 may be unlabeled and/or smooth. In the sensor 100 shown in FIGS. 1A and 1B, a portion of the waveguide's outer surface 112 runs roughly parallel to the surface of the silicon substrate 130.

FIGS. 1A and 1B also show that the pedestal 120 has a rectangular cross section with a width d and a height s. These dimensions may be selected for ease of fabrication, and/or to provide desired performance. For instance, the pedestal width d may be about 0.5 µm to about 2.5 µm (e.g., 0.75 µm, 1.0 µm, 1.25 µm, 1.5 µm, 1.75 µm, 2.0 µm, or 2.25 µm), and the pedestal height s may be about 1.0 µm to about 20 µm (e.g., 2.5 µm, 5.0 µm, 7.5 µm, 10.0 µm, 12.5 µm, 15.0 µm, or 17.5 µm). If desired, the pedestal may be smoothly tapered at its top and/or its bottom to provide increased stability and/or to reduce mechanical stress and strain on the sensor 100 and its components.

Because the sensor 100 is made of silicon with well-developed fabrication processes and a wide mid-IR transparency, it can accommodate broadband laser scanning, which is useful for multi-spectral and diverse chemical analysis. In addition, silicon is a rugged material in response to harsh environments, since it is chemically inert when exposed to most organic chemicals. Therefore, the fabricated sensors can be utilized in tracing a variety of organic pollutants.

Germanium Pedestal Waveguide Sensors

Figure 1C:
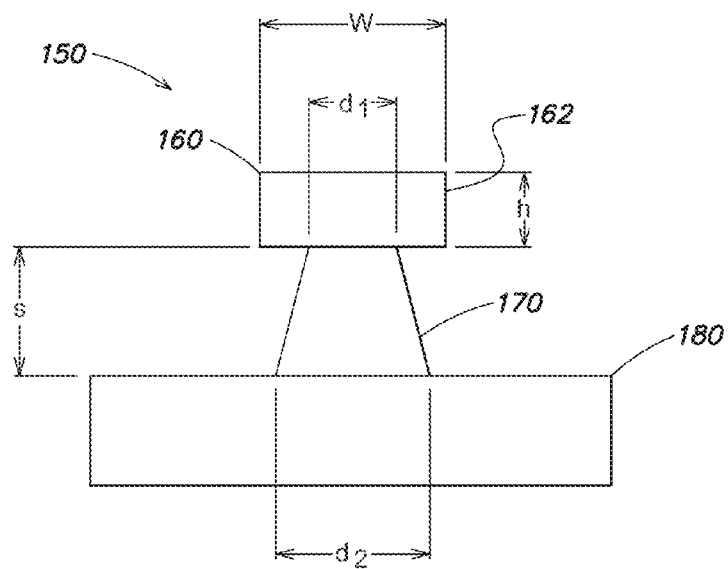
FIG. 1C is an end-on view of an exemplary air-clad, germanium pedestal waveguide suitable for mid-IR sensing with a waveguide width w, a waveguide height h, a pedestal height s, a pedestal upper base width $d_1$, and a pedestal lower base width $d_2$.
Figure 1D:
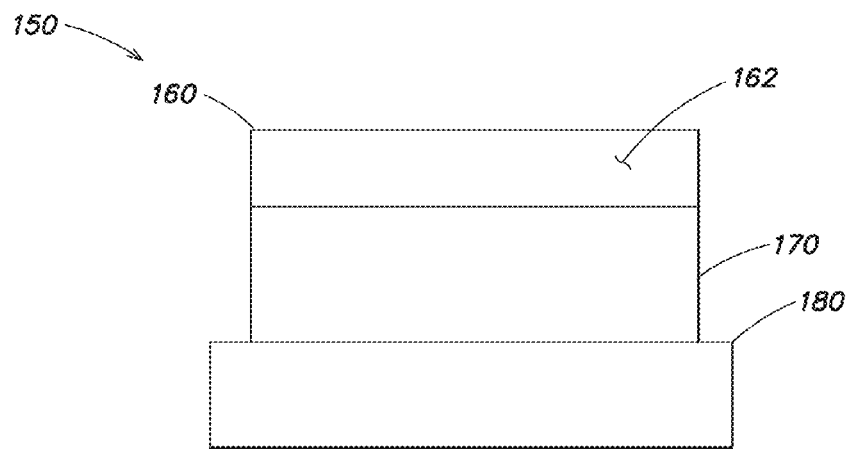
FIG. 1D is a side view of the germanium pedestal waveguide of FIG. 1C.

FIGS. 1C and 1D show a sensor 150 that includes a mid-IR germanium waveguide 160 on a silicon pedestal 170 extending from a silicon wafer (substrate) 180. Like the silicon sensor 100 shown in FIGS. 1A and 1B, the sensor 150 shown in FIGS. 1C and 1D can be used to detect the presence of analytes on or close to (e.g., within one wavelength of) the waveguide's outer surface 162 via attenuation of the evanescent wave extending from the waveguide 160, Germanium's broad mid-IR transparency, which can extend up to $\lambda=12$ µm, makes the germanium-based sensor 150 particularly useful for on-chip chemical sensing (finger-printing spectrometry) of double-bond functional groups, including C═O, C═N and C=C, that exhibit vibrational absorption between λ=5 µm and λ=12 µm. Germanium is also compatible with CMOS processes and exhibits robust mechanical and chemical properties.

As readily understood by those of skill in the art, however, the waveguide's shape and dimensions may be selected to support propagation of one or modes of a mid-IR electromagnetic wave. For example, FIG. 1C shows the germanium waveguide 160 as having a rectangular cross section with a width w and a height (thickness) h. (In some cases, the top of the waveguide 160 may bulge slightly as described below with respect to FIGS. 21A-21D.) Depending on the embodiment, the waveguide width w may be about 1 µm to about 30 µm (e.g., 2.5 µm, 5.0 µm, 7.5 µm, 10.0 µm, 12.5 µm, 15.0 µm, 17.5 µm, 20.0 µm, 22.5 µm, 25.0 µm, or 27.5 µm) and the waveguide height h may be about 1 µm to about 30 µm (e.g., 2.5 µm, 5.0 µm, 7.5 µm, 10.0 µm, 12.5 µm, 15.0 µm, 17.5 µm, 20.0 µm, 22.5 µm, 25.0 µm, or 27.5 µm). Other embodiments may have different cross-sectional shapes, including but not limited to circles, triangles, squares, pentagons, hexagon, octagons, etc.

In some cases, the germanium waveguide's shape and dimensions may be chosen to support propagation of only a single mode (e.g., the $TEM_{00}$ mode) of a beam with a wavelength of about 2 µm to about 12 µm (e.g., about 5 µm to about 12 µm). In other cases, the germanium waveguide's shape and dimensions may be chosen to support propagation of multiple modes at mid-IR wavelengths. If desired, the germanium waveguide 160 may include stress members and/or have a shape or composition selected to preserve the polarization state of the mid-IR beam propagating through the germanium waveguide 160. In other words, the germanium waveguide 160 may be a polarization-maintaining waveguide as readily understood by those of skill in the art.

Depending on the embodiment, the germanium waveguide's shape and dimensions may also be chosen to support an evanescent wave (tail) that extends laterally out of the germanium waveguide 160 through its outer surface 162. In operation, at least a portion of the evanescent wave may be absorbed by one or more molecules within a length about equal to the evanescent wave's decay constant. For instance, the molecule(s) may absorb one or more of the evanescent wave's spectral components, leading to a spectrally selective reduction in intensity of the wave propagating through the germanium waveguide 160. Detecting this spectrally selective reduction in intensity—e.g., by measuring the absorption spectrum—at the waveguide's output yields an indication of the type and concentration of molecules in the fluid surrounding the germanium waveguide 160.

In some examples, the germanium waveguide's outer surface 162 may be configured to receive or support at least one molecule (e.g., an organic molecule) in fluid surrounding the germanium pedestal waveguide sensor 150. For instance, the outer surface 162 may be textured, patterned, and/or coated to promote adhesion of the molecules to the outer surface 162. In other cases, the outer surface 162 may be unlabeled and/or smooth. In the sensor 150 shown in FIGS. 1C and 1D, a portion of the waveguide's outer surface 162 runs roughly parallel to the surface of the silicon substrate 180.

FIGS. 1C and 1D also show that the germanium waveguide 160 sits atop a silicon pedestal 170 whose cross section is in the shape of an isosceles trapezoid. The silicon pedestal's cross section has an upper base width $d_1$, a lower base width $d_2$, and a height s measured perpendicular to the upper and lower bases. The base angle formed between the lower base and the sides may about 54.7° due to anisotropic etching of the (100) and (111) planes of crystalline silicon during fabrication. The pedestal's dimensions may be selected for ease of fabrication, and/or to provide desired performance. For instance, the pedestal's upper base width $d_1$ may be selected to prevent or promote confinement of the TM mode within the pedestal 170 itself. In some cases, the pedestal's upper base width $d_1$ may be about 0.1 µm to about 2.5 µm (e.g., 0.25 µm, 0.5 µm, 0.75 µm, 1.0 µm, 1.25 µm, 1.5 µm, 1.75 µm, 2.0 µm, or 2.25 µm). And the pedestal height s may be about 0.4 µm to about 50 µm (e.g., 0.5 µm, 1.0 µm, 1.5 µm, 2.0 µm, 2.5 µm, 5.0 µm, 7.5 µm, 10.0 µm, 12.5 µm, 15.0 µm, 17.5 µm, 20 µm, 25 µm, 30 µm, 35 µm, 40 µm, or 45 µm) depending on the application and the etch ratio of (100) to (111) semiconductor planes. The exact sizes and shapes of the mid-IR germanium waveguide 160 and the silicon pedestal 170 can be designed and optimized, e.g., using two-dimensional finite element method (FEM) and Finite Difference Time Domain (FDTD), to achieve a particular mode profile/confinement as explained in greater detail below.

Mid-IR Sensor on a Chip

Figure 2:
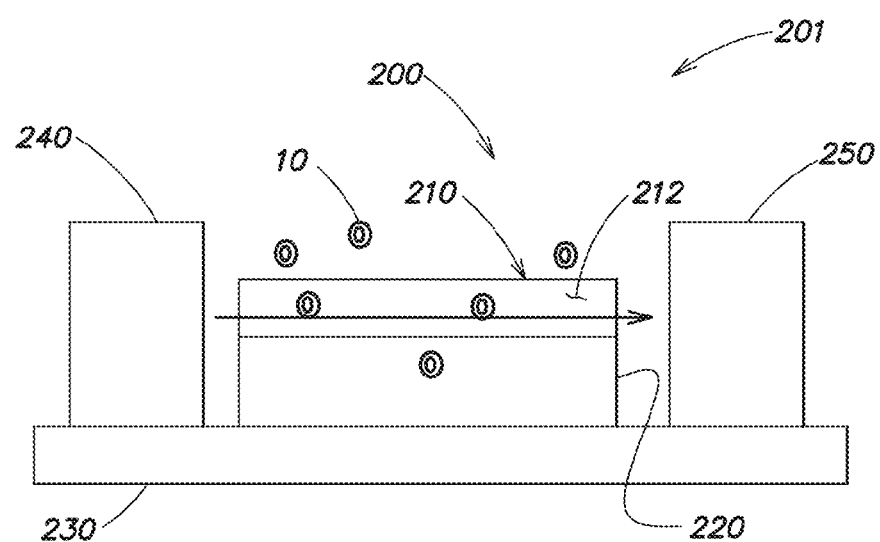
FIG. 2 is a schematic diagram of a chip-based mid-IR sensor that includes a semiconductor pedestal waveguide (e.g., the silicon pedestal waveguide of FIGS. 1A and 1B or the germanium pedestal waveguide of FIGS. 1C and 1D).

FIG. 2 shows a chip 201 that includes a semiconductor pedestal waveguide sensor 200 (e.g., a silicon or germanium sensor) integrated with a light source 240 and a detector 250 onto a semiconductor substrate 230 (e.g., a silicon substrate). In operation, the light source 240, which may include one or more narrowband/coherent emitters (e.g., quantum cascade lasers), broadband emitters, or tunable emitters, emits a beam of mid-IR light. For instance, the light source 240 may emit a beam whose wavelength spans or is tuned over some or all of the mid-IR portion of the electromagnetic spectrum, e.g., over a bandwidth of about 1.0 µm to about 12.0 µm (e.g., about 2 µm, 3 µm, 4 µm, 5 µm, 6 µm, 7 µm, 8 µm, 9 µm, 10 µm, or 11 µm). In operation, the light emitted by the light source 240 is coupled into a semiconductor waveguide 210, such as a silicon or germanium waveguide, in the sensor 200, e.g., via butt-coupling or with one or more lenses (not shown). Another lens (not shown) may focus light emitted by the waveguide 210 onto the detector 220.

In operation, the sensor 200 on the chip 201 is exposed to a fluid (e.g., gas or liquid) to be analyzed for the presence (or absence) of one or more particular chemicals or compounds. For instance, the fluid may be a liquid that is dropped onto the chip 201 with a pipette. The chip 201 may also be immersed in fluid or placed in a fluid flow. If desired, the chip 201 may be integrated with one or more micro-fluidic devices to prevent evaporation and improve device stability.

At least some of the fluid extends over or near at least a portion of the sensor's waveguide 210. As light from the light source 240 propagates through the waveguide 210, the fluid may absorb some or all of one or more spectral components of the evanescent tail extending from the waveguide's exterior surface 212. This absorption reduces the intensity of the corresponding spectral component(s) of the mode propagating through the waveguide 210, producing a variation in the intensity of at least one spectral component of the beam emitted by the waveguide 210.

The detector 250 senses this spectrally selective variation in intensity of the emitted beam and emits a photocurrent or other electrical signal whose amplitude is proportional to the intensity of the emitted beam. The detector 250 may include one or more broadband sensing elements and/or spectrally selective narrowband sensing elements. For instance, the detector 250 may include a spectrometer formed by a grating or other dispersive element that directs different spectral components of a broadband beam into different angles, each of which is monitored by a respective detector element in a detector array (e.g., a charged coupled device (CCD) or complementary metal-oxide-semiconductor (CMOS) sensing array) to yield the absorption spectrum of the absorbers evanescently coupled to the sensor 200. Alternatively, the detector 250 may include a single sensing element that detects the time-varying intensity of a spectrally swept (chirped) beam. Mapping the resulting time-varying intensity signal to the spectral sweep speed yields an absorption spectrum that can be used to identify any absorbers evanescently coupled to the sensor 200.

The chip 201 can be used to identify chemicals from an unknown solution by using the detected absorption spectrum as a chemical "fingerprint." In some cases, the wavelength of the probe beam emitted by the light source 240 may be tuned or chosen based on known characteristic absorption bands to monitor a fluid for one or more particular chemicals. For instance, hexane has a distinguishable higher absorbance at $\lambda=3.55\,\mu m$, so tuning the probe light to this wavelength yields a signal that can be used to detect hexane relatively easily. Likewise, to detect a compound that includes an amine functional group, the probe beam's wavelength may be between $\lambda=2.85\,\mu m$ and $\lambda=3.22\,\mu m$ to interrogate absorption from the N H stretch associated with the amine functional group.

Fabricating a Silicon Pedestal Waveguide

FIGS. 3A-3F illustrate a process 300 for making a silicon pedestal waveguide, such as the waveguide 100 shown in FIGS. 1A and 1B, that involves dry/wet etching and conformal oxide deposition. In FIG. 3A, photoresist 330 is deposited onto a thermal oxide layer 320 (e.g., a $SiO_2$ layer, other oxide layer, or nitride layer), which in turn is on a silicon wafer 310 (e.g., a 3 μm thick oxide-on-silicon wafer). As understood by the those of skill in the art, the photoresist 330 may be patterned using photolithography to form a straight waveguide, curved waveguide, splitter, ring, or group of waveguides. Once the photoresist 330 is patterned as desired, the patterns are transferred sequentially into the thermal oxide layer 320 and the silicon wafer 310 using inductively coupled plasma reactive ion etching (ICP-RIE), wet anisotropic patterning, or any other suitable type of anisotropic etching to form a silicon ridge 312 coated with an oxide layer 320 as shown in FIG. 3B. (This technique can also be used to form a gallium arsenide ridge or germanium.) For instance, to selectively remove oxide, a gas mixture composed of $H_2/CHF_3/CF_4$ may be used to obtain an etching depth of 3 μm in the thermal oxide layer 320. And to selectively remove silicon, a $C_4F_8/SF_6$ gas mixture can be used to obtain an etching depth of 10 μm in the silicon wafer 310.

In FIG. 3C, a thin oxide layer 340 (comprising, e.g., silicon dioxide, another oxide, or a nitride) with a thickness of about 0.5 μm to about 3.0 μm is conformally deposited on the oxide-coated silicon ridge 312 using plasma-enhanced chemical vapor deposition (PECVD) or any other suitable deposition technique. Suitable materials for the thin oxide layer 340 include silicon dioxide, other oxides (e.g., thermal oxide), and nitrides. The thin oxide layer 340 is anisotropically and preferentially etched back using ICP-RIE as shown in FIG. 3D. More specifically, the thin oxide layer 340 is etched back to reveal at least a portion of the silicon wafer's horizontal surface(s) and the thermal oxide layer's horizon surface(s), and to leave a vertical oxide layer 342 on the silicon ridge's vertical sidewall to protect the sidewall's surface.

Once the thin oxide layer 340 has been etched back, the silicon ridge 312 is undercut, e.g., using isotropic etching with $SF_6$ gas, to form the sensor's waveguide 110 and the pedestal 120 as shown in FIG. 3E. This isotropic etching removes only silicon that is not covered by an oxide (thermal oxide layer 320 and thin oxide layer 340). The remaining oxide may then removed by a buffered oxide etch (BOE) to reveal the completed sensor 100, which has a waveguide width w, waveguide height h, lift-off length s, and notch width d as shown in FIG. 3F. These four parameters affect the waveguide's performance, and can be modified or selected by changing the associated pattern design or by alternative etching methods.

Figure 4D:
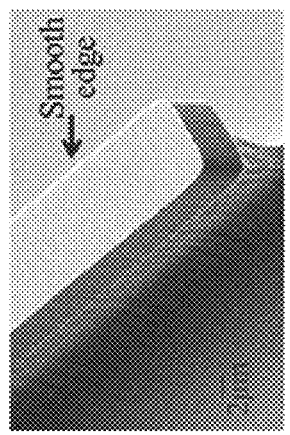
FIG. 4D is an SEM image of the waveguide of FIG. 4A, taken at an angle of 45°, to inspect the waveguide's smooth sidewall.

FIGS. 4A-4F are scanning electron microscope (SEM) images of fabricated mid-IR waveguides, which are tilted at 54° during microscopy to improve the cross-sectional view. FIG. 4A shows an array of parallel waveguides; FIG. 4B is a close-up of the middle waveguide in FIG. 4A that shows that the structure dimensions are w=8 μm, h=5 μm, s=14 μm, and d=2 μm. FIGS. 4A and 4B also show that the waveguide edges (top of the structure) are smooth (no bumps or indentations appear in the pictures) and straight (no bending or distortion is observed), and that the waveguide structure is well resolved (no cracks or roughness appear on the waveguide edges). This indicates that silicon pedestal structures are successfully created by the fabrication process illustrated in FIGS. 3A-3F.

Figure 4F:
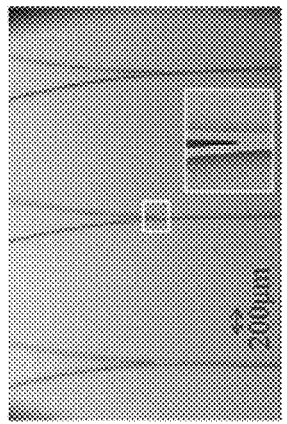
FIG. 4F is an SEM image of an array of forked silicon pedestal waveguides (the inset shows a magnified view of the fork (splitter) in the middle waveguide).
Figure 4C:
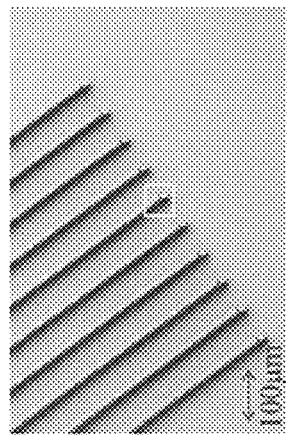
FIG. 4C is another SEM image of the array of FIG. 4A (the box indicates the view shown in FIG. 4D).

FIG. 4C shows the waveguide array of FIG. 4A rotated by 45° to visualize the morphology of the waveguide sidewalls. FIG. 4D is an enlarged image of the region indicated by the rectangle in FIG. 4C. FIG. 4D shows that no defects appear in the vertical facets, confirming that the conformally deposited oxide layer protected the waveguide cores during the isotropic silicon etching. FIG. 4D also shows that the waveguide edges are smooth and straight.

Figure 4E:
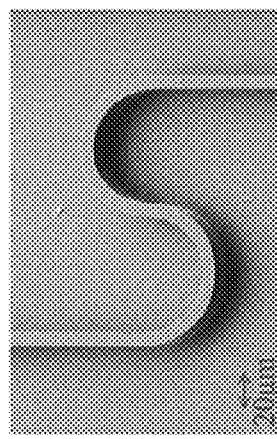
FIG. 4E is an SEM image of a curved section of a silicon pedestal waveguide.

FIG. 4E is an image of an individual waveguide with two regions that are bent to form a paper clip shape. Each bent region's radius of the curvature is about 50 μm. FIG. 4E shows that the strip (pedestal) underneath the waveguide supports the waveguide well. Other shapes and bend radii are also possible; for instance, the pedestal waveguide can be formed in an arc, undulating curve, sinusoid, or ring. For instance, the waveguide can be formed into a Y-shaped splitter with gently curved arms extending from a single waveguide as shown in FIG. 4F. The magnified image in the inset of FIG. 4F shows that the splitter region has a highly symmetric structure for achieving a 50/50 power splitting ratio. Other splitting ratios (e.g., 90/10 and 95/5) are also possible, as are splitters with multiple ports (e.g., n×m splitters, where n and m are positive integers). The splitter may also be tunable, e.g., via one or more heaters that heat the waveguide(s) so as to modulate their refractive indices.

Characterizing Silicon Pedestal Waveguides

Figure 5A:
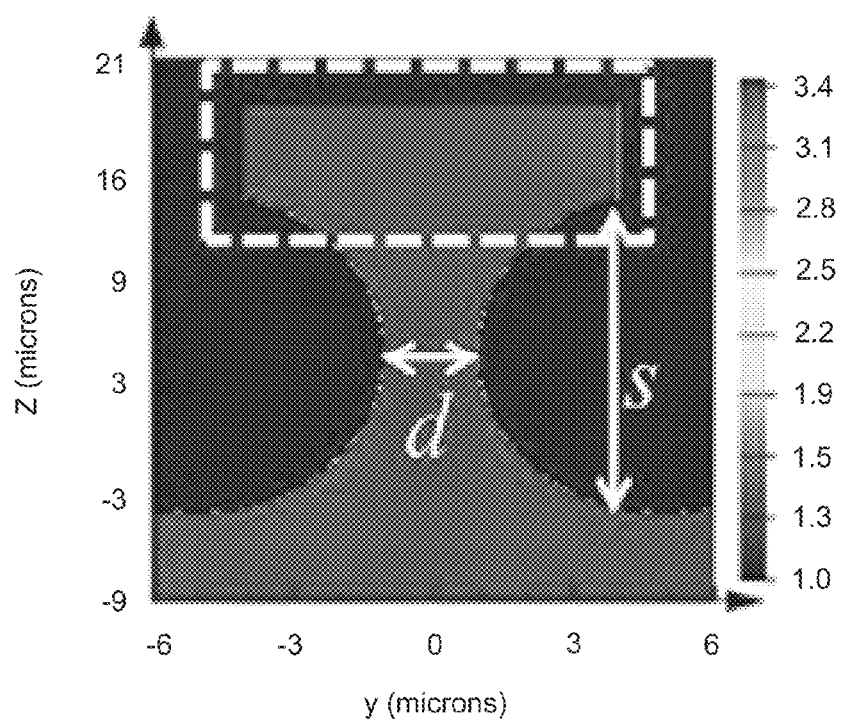
FIG. 5A is a plot of the refractive index profile of a silicon pedestal waveguide structure used for finite-difference simulations of waveguide performance (the dashed box indicates the light source used to couple light into the waveguide).
Figure 5B:
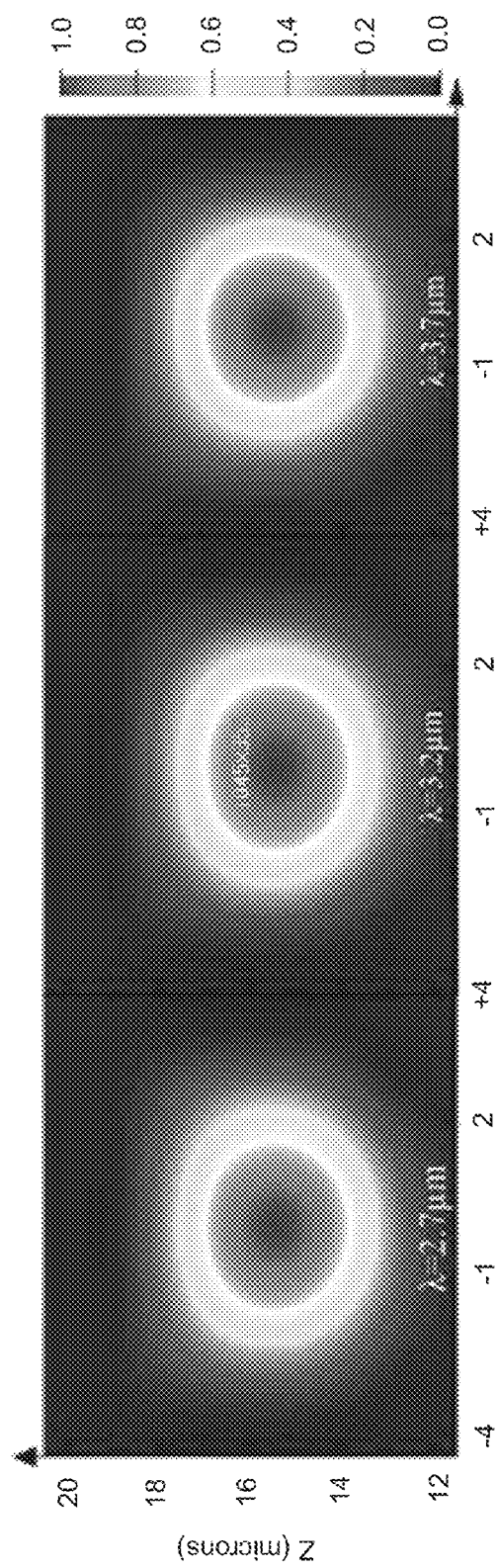
FIG. 5B illustrates simulated field profiles of the silicon pedestal waveguide of FIG. 5A guiding light at wavelengths of $\lambda=2.7$ μm (left), $\lambda=3.2$ μm (center), and $\lambda=3.7$ μm (right).

FIGS. 5A and 5B illustrate two dimensional finite difference method (FDM) simulations of an exemplary silicon pedestal waveguide's light-guiding performance in the mid-IR spectral range. FIG. 5A illustrates the pedestal configuration used in the FDM modeling. The structure dimensions are w=8 μm, h=5 μm, s=14 μm, and d=2 μm, which match the device dimensions experimentally observed from the SEM characterization in FIGS. 4A and 4B. A light source of 9 μm×9 μm is chosen so its size is comparable to a single-mode fiber with 9 μm core diameter. FIG. 5B shows the field profiles (intensity versus lateral dimension) of the air-clad waveguide mode are calculated at $\lambda=2.7$ μm (left), $\lambda=3.2$ μm (center), and $\lambda=3.7$ μm (right). FIG. 5B shows that a fundamental mode is clearly resolved where the lightwave is highly confined inside the upper silicon waveguide. In addition, FIG. 5B shows that negligible variation is observed in the mode profiles when the wavelength is scanned over a broad spectral range. FIG. 5B also shows that a portion of the mode profile extends beyond the waveguide's edges to enhance the interaction with the fluid/chemical analyte being monitored.

Figure 6:
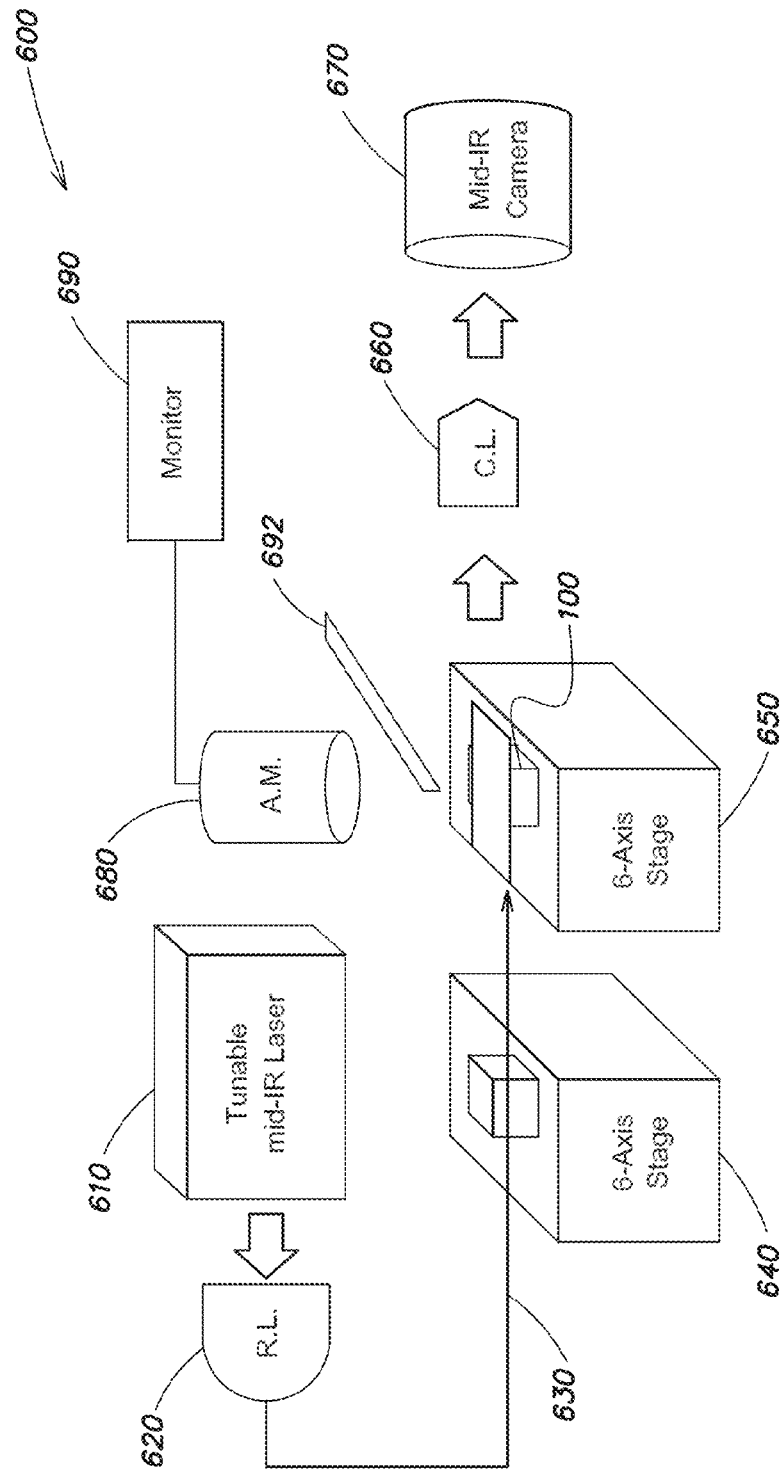
FIG. 6 is a schematic diagram of a system suitable for characterizing mid-IR sensing with a silicon pedestal waveguide.

FIG. 6 illustrates a system 600 for evaluating the performance of silicon pedestal waveguides and splitters such as those shown in FIGS. 1A and 1B. The system 600 includes a tunable mid-IR laser 610 that emits a pulsed laser beam with an average power of about 150 mW that can be tuned over a wavelength range of about $\lambda=2.4$ µm to about $\lambda=3.7$ µm. The pulsed laser beam is coupled into a mid-IR fluoride fiber 630 with a 9 µm core and 125 µm cladding using a reflective lens 620. In operation, the reflective lens 620 collimates the pulsed laser beam, then butt couples the collimated beam into the fiber 630. The mid-IR fiber 630 extends onto a first six-axis stage 640, which can be used to align the mid-IR fiber's core with the smooth, cleaved front facet of the silicon waveguide 100. If desired, the silicon waveguidge 100 can be mounted on a second six-axis stage 650 to provide additional degrees of freedom.

Light propagates through waveguide 100 and may be evanescently absorbed by an analyte delivered with a pipette 692 or other fluid delivery device (e.g., a microfluidic channel). A calcium fluoride biconvex lens 660 at the waveguide's output focuses the light emitted by the waveguide 660 onto the active area of a mid-IR camera 670, such as a liquid nitrogen cooled 320 pixel×256 pixel InSb camera or other suitable mid-IR detector, which produces a photocurrent or other electrical signal whose amplitude is proportional to the intensity of the detected mid-IR radiation.

The system 600 also includes a microscope 680 with a long working distance objective for fine adjustment of the fiber's tip with respect to the waveguide 100. The microscope 680 projects a magnified image of the waveguide 100 onto a monitor 690 for use in aligning the mid-IR fiber 630, the waveguide 100, and/or the mid-IR camera 670 with respect to each other. For instance, the alignment between the fiber 630 and the waveguide 100 can be performed under microscope guidance using the positioning stages 640 and 650, which provide full control of six axes (x, y, z, θ, ψ, φ) with 0.02 µm sensitivity.

Mode Profiles and Transmittance of a Broadband Mid-IR Waveguide

Figure 7:
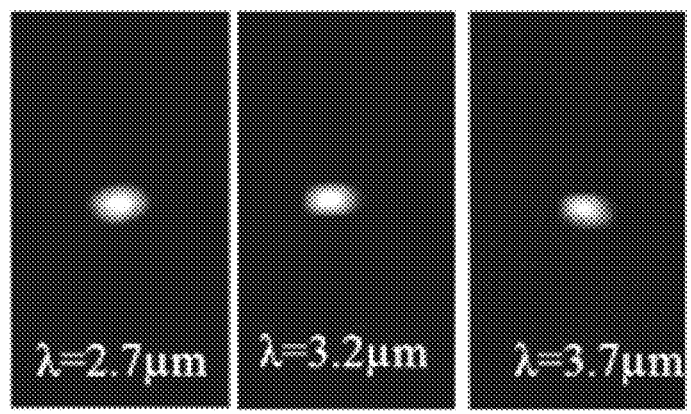
FIG. 7 shows mode profiles of silicon pedestal waveguides captured by a mid-IR camera at wavelengths of $\lambda=2.7$ μm (left), $\lambda=3.2$ μm (center), and $\lambda=3.7$ μm (right).

FIG. 7 shows images captured with a mid-IR camera of the waveguide modes of a silicon pedestal waveguide guiding light at wavelengths of $\lambda=2.7$ µm (left), $\lambda=3.2$ µm (center), and $\lambda=3.7$ µm (right). Each image shows a sharp, clearly resolvable fundamental mode as predicted by the FDM simulation. No scattering or distortion appears in FIG. 7, which implies that the mid-IR probe light is confined inside the silicon pedestal waveguide. Furthermore, the images show that the fundamental mode remains dominant within a wide spectral range, indicating that a silicon pedestal waveguide can efficiently deliver broadband mid-IR signals on-chip.

Figure 8:
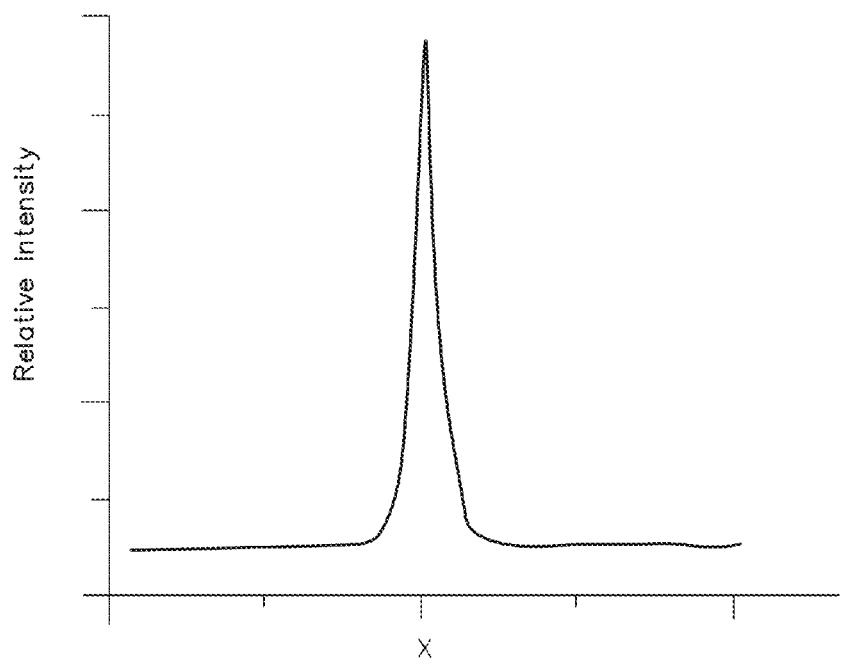
FIG. 8 is a plot of measured optical power (dots) and a curve fit (line) versus wavelength for silicon pedestal waveguides (inset) with different relative length D.

FIG. 8 is a plot of the intensity profile of the mode image captured at $\lambda=3.3$ µm (FIG. 7, center). Like FIG. 7, FIG. 8 shows that a sharp fundamental mode is clearly resolved without scattering or distortion, which implies that the mid-IR probe light is well confined inside the silicon pedestal waveguides as predicted by the simulation. FIG. 8 also shows that the full-width half-maximum (FWHM) of the fundamental mode is roughly equal to about two-fifths of the waveguide size.

If desired, the profile of an exemplary waveguide's fundamental mode can be evaluated over a wide range of operating wavelengths (e.g., 1.0-8.0 µm, 1.3-6.5 µm, 2.7-3.7 µm, etc.). The resulting measurements can be used to set the sensor's baseline transmittance profile as a function of wavelength (in other words, a baseline spectral profile) for use in chemical sensing and monitoring, among other applications. For instance, the baseline transmittance can be subtracted from a raw signal provided by a photodetector to account for spectrally dependent variations in the source's output, the waveguide's absorption, and/or the detector's responsivity. Subsequent profile evaluations can be used to track and account for changes can caused by changes in the sensor's performance due to aging, temperature changes, pressure changes, etc.

Figure 9:
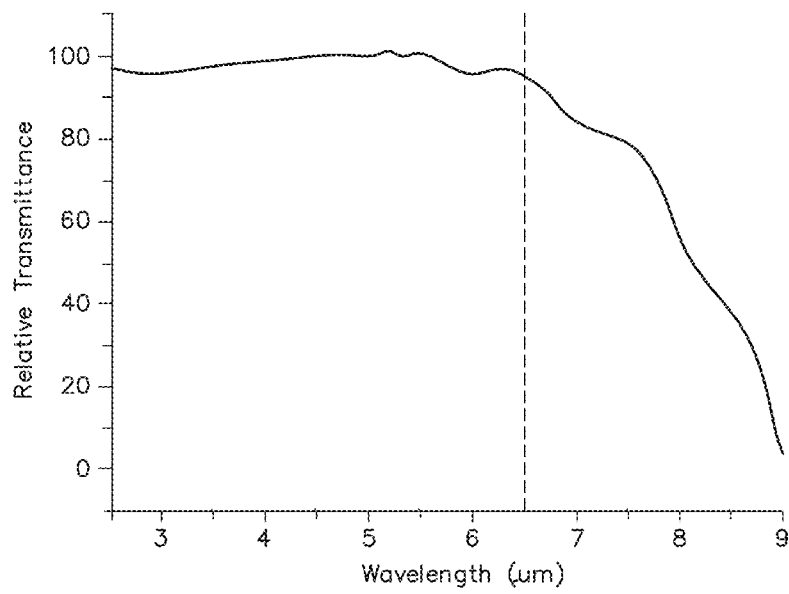
FIG. 9 is a plot of the measured transmission spectrum of an exemplary fabricated crystalline silicon-based sensor platform (the dashed line indicates relatively high transparency up to $\lambda=6.5$ μm).

FIG. 9 shows the transmission spectrum of a silicon-based pedestal waveguide measured at normal incidence from $\lambda=2.5$ µm to $\lambda=9$ µm by Fourier transform infrared spectroscopy (FTIR). The data shown in FIG. 9 represent the average of 20 measurements with a scanning resolution of 4 cm$^{-1}$. FIG. 9 shows that the sensor platform remains transparent over a large portion of the mid-IR spectrum; as a result, its operational spectral range is large enough for broadband mid-IR sensing with good transparency. No significant reduction of optical transmittance occurs below $\lambda=6.5$ µm. Without being bound by any particular theory, the decrease of transmittance observed above $\lambda=6.5$ µm may be due to multiphonon absorption.

Figure 10:
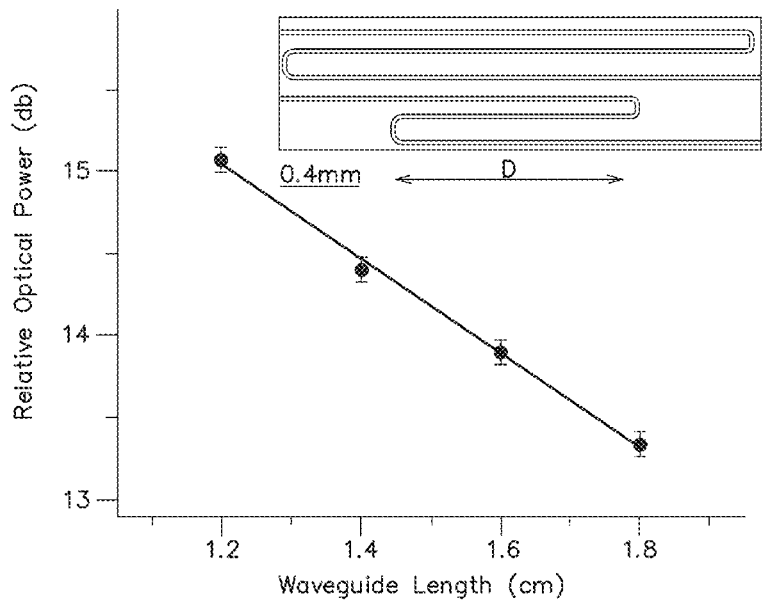
FIG. 10 is a plot of relative optical power measurements (circles with error bars) versus waveguide length for the paperclip-shaped pedestal waveguide shown in the inset of FIG. 10.

FIG. 10 is a plot of relative optical power measurements (circles) versus waveguide length for the paperclip-shaped pedestal waveguide shown in the inset of FIG. 10. The error bars indicate a measurement error of less than 0.15 dB/cm. The paper clip center distance D varies from about 1 mm to about 4 mm, which corresponds to a variation in waveguide length from about 2 mm to about 8 mm. Fitting the length-dependent optical powers measured at each waveguide output yields a diagonal line with a slope corresponding to an optical loss of as low as 2.7 dB/cm at a wavelength of $\lambda=3.7$ µm. These results show that examples of the silicon pedestal structures disclosed herein guide mid-IR light efficiently compared to waveguides with lossy oxide claddings, which attenuates light considerably at wavelengths above about 3.6 µm.

Figure 11A:
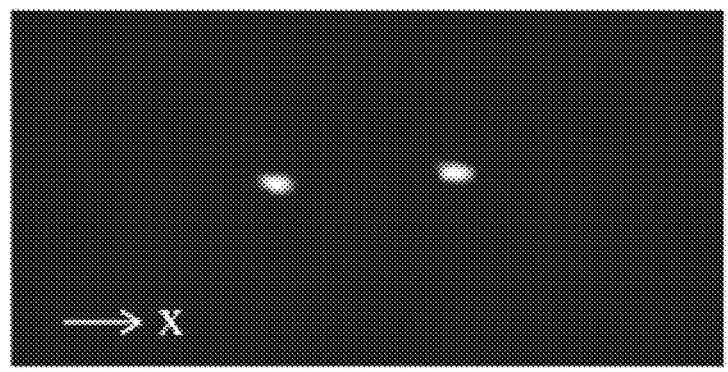
FIG. 11A is a mid-IR image of modes propagating out of a Y-branch waveguide splitter guide at $\lambda=3.2$ μm.
Figure 11B:
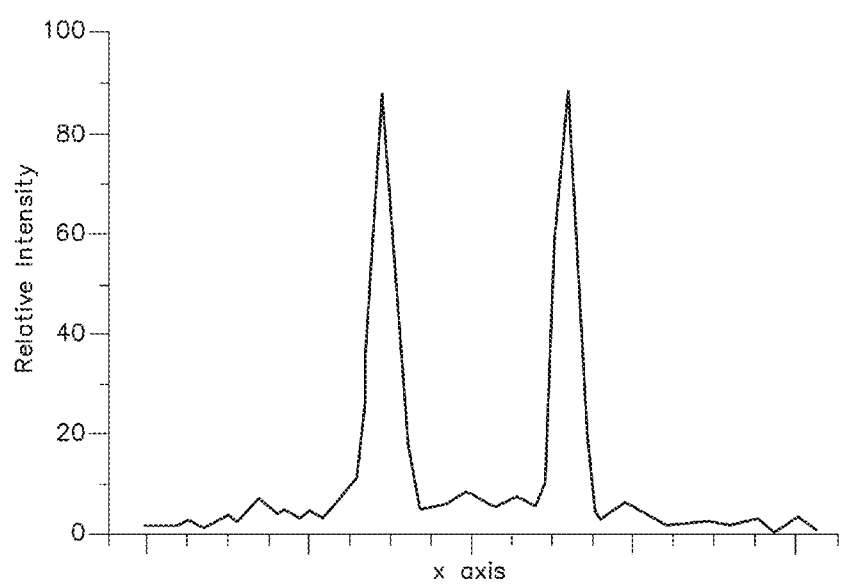
FIG. 11B is a plot of the relative intensity versus lateral dimension across the x axis of the modes illustrated in FIG. 11A.

FIGS. 11A and 11B illustrate the performance of a Y-branch silicon waveguide splitter supported by a pedestal structure (e.g., as shown in FIG. 4F). FIG. 11A is a mid-IR image of the output of a splitter that guides light at $\lambda=3.2$ µm. It shows two sharp spots arising, respectively, from a fundamental mode from each arm of the waveguide splitter. No other modes are visible, which indicates that higher-order modes are not excited appreciably, if at all, when the guided wave propagates through the input single-arm into the output double-arms. FIG. 11B is a plot of the intensity profile (relative intensity versus transverse dimension) measured across the x axis indicated in FIG. 11A. It shows two peaks with similar shapes and nearly identical maximum intensities, which indicates that the splitting ratio is 50/50. The beam splitter can be used to couple light into multiple waveguide channels, e.g., for use in mid-IR planar array devices.

Mid-IR Measurements of Selected Solvents

To demonstrate quantitative chemical sensing, air-clad pedestal Si waveguides were used to evaluate organic solutions of differing concentrations (by weight), including methanol, toluene, hexane, carbon tetrachloride, and acetone (≥99.9%). Each of these solutions has a different absorption spectrum; for example, toluene absorbs light strongly at a wavelength of $\lambda=3.3$ µm due to the aromatic C—H stretch, whereas carbon tetrachloride has no C—H bond and does not absorb light appreciably, if at all, at $\lambda=3.3$ µm. In each test, 1 mL of solution was dropped from a glass pipette onto a mid-IR silicon pedestal waveguide sensor array with 1 cm$^2$ surface area to ensure the entire array was fully covered by the solution. The intensity of the beam transmitted through the waveguide, which was kept at a temperature of 25° C., was measured using the system shown in FIG. 6.

Figure 12:
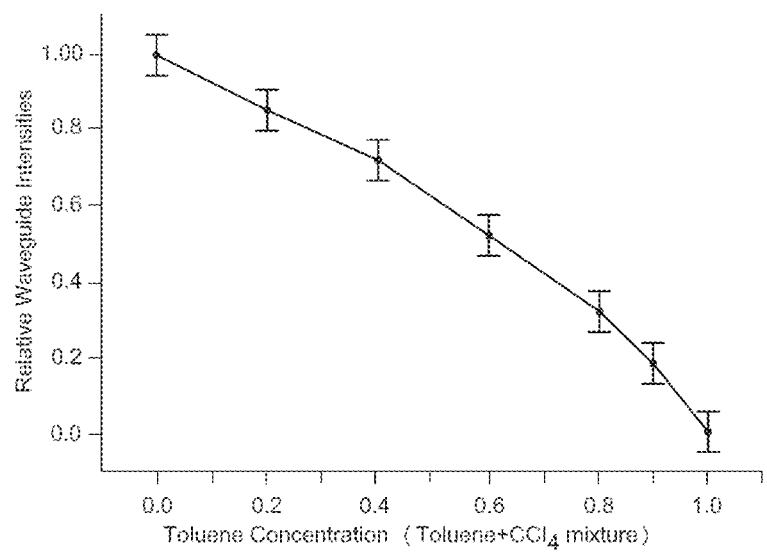
FIG. 12 is a plot of waveguide mode intensities at different toluene/$CCl_4$ concentrations showing a decrease in intensity with increasing toluene ratio due to mid-IR absorption from the aromatic C—H stretch in toluene.

FIG. 12 is a plot of toluene concentration (by weight) in carbon tetrachloride versus waveguide mode intensity measured using a mid-IR sensor in the set-up of FIG. 6. FIG. 12 shows that increasing the toluene concentration from 0 to 1 causes the light intensity measured at the output end of the waveguide to decrease monotonically, which indicates that the sensor can be used to distinguish different concentrations. Without being bound by any particular theory, the evanescent light from the Mid-IR waveguide is absorbed by the surrounding chemical analyte molecules of interest, and consequently the intensity of the guided light decreases. The change in intensity is proportional to the analyte concentration and reveals quantitative information regarding the concentration of the chemical.

Figure 13:
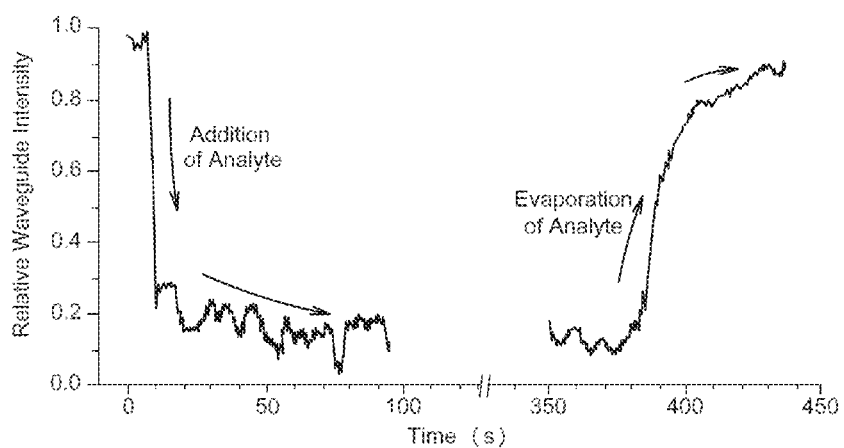
FIG. 13 is a real-time trace of intensity change over time measured at the output of a mid-IR silicon pedestal waveguide sensor exposed to toluene.

FIG. 13 is plot of a measurement of an exemplary waveguide's transient response to toluene at a wavelength of $\lambda=3.3$ μm. The time-resolved response of mid-IR detection was obtained by recording the waveguide's transmitted intensity upon exposure to toluene. The transmitted intensity dropped instantly as the analyte reached the sensor, where the intensity variation is indicated by the arrows. The intensity decreased as the toluene interacted with the waveguide mode. After about 5 seconds, the toluene covered the entire surface of the sensor and the signal stabilized due to the toluene's absorption of the mid-IR evanescent wave. The waveguide intensity remained stable and low until most of the toluene evaporated at between about 370 seconds and about 400 seconds, at which point the transmitted intensity increased sharply. The increase in intensity became slower after about 400 seconds because the surface tension at the toluene-silicon interface caused a thin toluene layer to remain on the waveguide. Eventually the intensity recovered to the original intensity at 0 seconds after complete evaporation of the toluene from the sensor surface. The sensor's response to the transient characteristics of the toluene solvent demonstrates that an exemplary sensor can monitor a chemical analyte in situ for applications including pollution control and early alarm systems.

Figure 14:
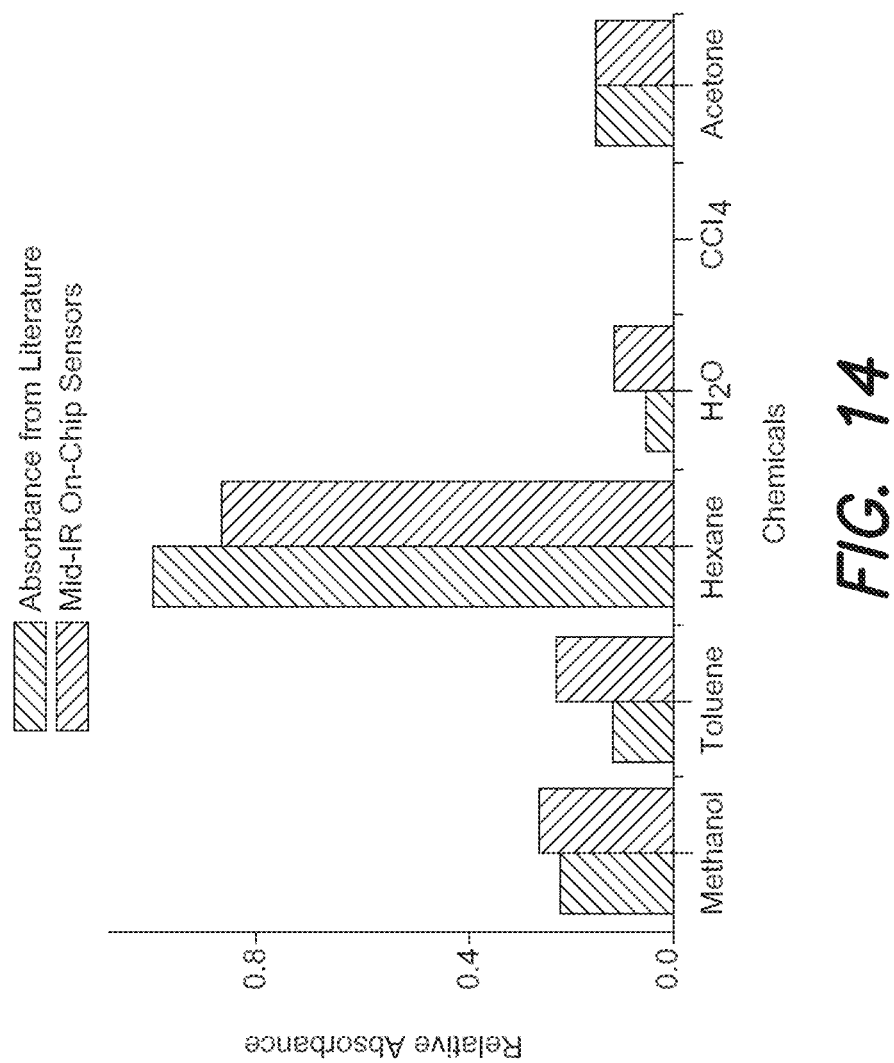
FIG. 14 is bar chart illustrating chemical sensing measurements made at $\lambda=3.55$ μm using an on-chip, mid-IR silicon pedestal waveguide sensor and absorbance measurements reported in the scientific literature.

FIG. 14 is a bar chart that illustrates the mid-IR sensor's ability to screen chemicals. It shows relative absorbance measurements for methanol, toluene, hexane, water ($H_2O$), carbon tetrachloride ($CCl_4$), and acetone made at a probe wavelength of $\lambda=3.55$ μm with an exemplary silicon pedestal waveguide sensor (left-hand bars). FIG. 14 also shows the absorbance for each chemical reported in the scientific literature (right-hand bars). The results show measurable differences in absorbance between these chemicals, and the trends agree well with reported results. Minor differences between the theory and the experiment may be due to the change of evaporation rates between different analytes. Using a sealed chamber or microfluidics should be able to resolve any error due to differences in evaporation rate.

Among other things, the results show the absorbance for hexane that corresponds to the symmetric stretch of the $CH_2$ group at $\lambda=3.5$ μm. On the other hand, methanol, toluene, and acetone have relatively low absorbance at $\lambda=3.55$ μm. The major absorbance peaks of toluene appear at $\lambda=3.45$ μm from the $sp^3$ C—H bond and $\lambda=3.33$ μm from the aromatic C—H bond. Methanol has major O—H absorbance at $\lambda=2.98$ μm and minor C—H stretch at $\lambda=3.45$ μm. Acetone has weak absorption from its $CH_3$ bond at $\lambda=3.3$ μm. As for water, absorption from the O—H stretch is positioned at $\lambda=2.76$ μm; for carbon tetrachloride, the asymmetric stretch of the C—Cl bond is beyond $\lambda=10$ μm. In other words, the major absorption peaks of water and carbon tetrachloride are far away from $\lambda=3.55$ μm, which explains why the sensor measured very low absorbance for these two chemicals at that wavelength.

Characterizing a Germanium Pedestal Waveguide

Simulation can also be used to characterize the performance of germanium-based waveguide sensors. For instance, a germanium waveguide can be simulated using FDTD to pick germanium waveguide and silicon pedestal parameters suitable for confining the guided mode(s) within the waveguide and preventing leakage of the mode into the silicon pedestal. The following examples examine three parameters of the waveguide/pedestal structures are optimized—pedestal width, waveguide thickness (height), and protrusion height—and two parameters of the mode supported by the waveguide.

Figure 15:
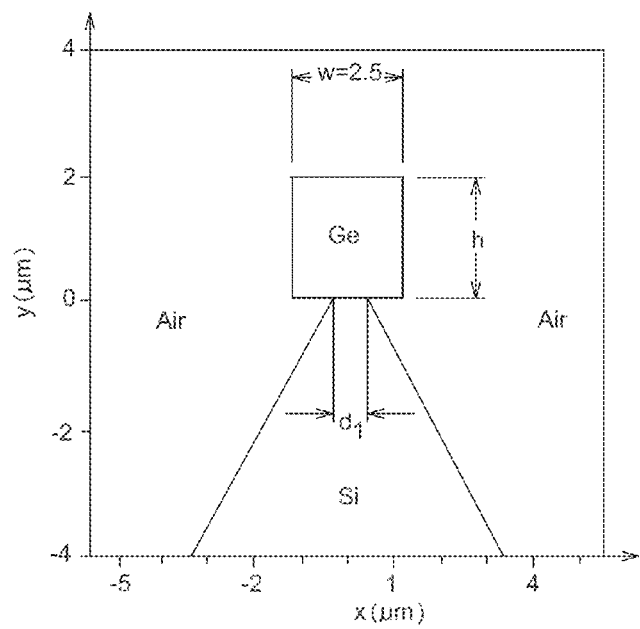
FIG. 15 shows a simulated refractive index profile along the cross section of a rectangular germanium waveguide with a width of w=2.5 μm and a height (thickness) h on a trapezoidal silicon pedestal with an upper base width $d_1$.

FIG. 15 shows the simulated refractive index profile of a rectangular germanium waveguide on an isosceles trapezoidal silicon pedestal. The waveguide has a height (thickness) h and a width set to w=2.5 μm, which matches the width shown in the SEM images of FIGS. 23A and 23B. The silicon pedestal has an upper base width $d_1$ and a base angle of about 54.7°. FIG. 15 shows that, at the wavelengths of interest (e.g., 3.1-3.7 μm), the silicon pedestal has a bulk refractive index of about 3.42-3.43 and the germanium waveguide has a bulk refractive index of about 4.02-4.04. The germanium waveguide and silicon pedestal are surround by a material with a refractive index of about 1.0 (e.g., air). This refractive index profile is used to generate the simulations shown in FIGS. 16-20.

Figure 16:
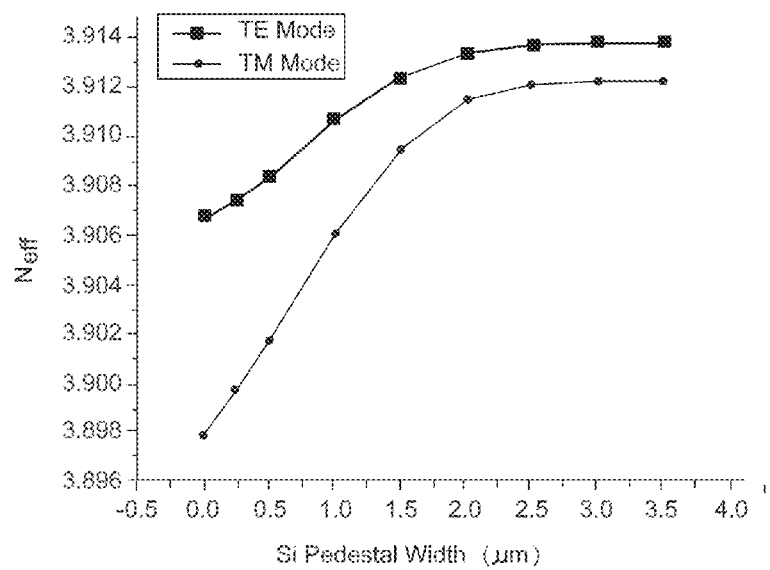
FIG. 16 is a plot of the effective mode index versus silicon pedestal top width $d_1$ for TE and TM modes guided in a germanium waveguide on a silicon pedestal.

FIG. 16 is a plot of the effective index of the confined mode, $N_{eff}$, calculated for both TE and TM modes at a wavelength of $\lambda=3.4$ μm. It shows that the effective index of the mode increases with increasing pedestal upper base width $d_1$ in increments of 0.25 μm from $d_1=0$ μm to $d_1=0.5$ μm and in increments of 0.5 μm from $d_1=0.5$ μm to $d_1=3.5$ μm. FIG. 16 also shows that the effective index of the TM mode increases more with increasing pedestal upper base width than the TE mode, which indicates that mode confinement in the vertical direction improves as pedestal upper base gets wider. It also indicates that the TM mode is more sensitive to changes in pedestal upper base width $d_1$ that the TE mode. Thus, the following simulations focus on the TM mode because it is more sensitive to changes in confinement in the vertical direction.

Figures 17A, 17B, 17C:
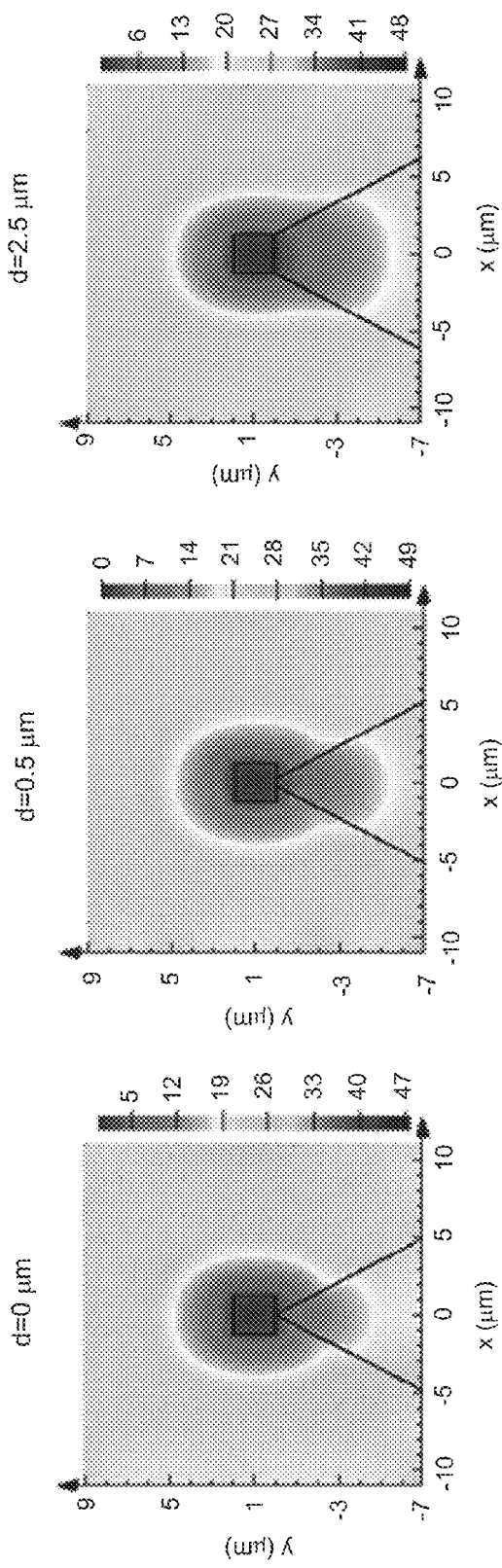
FIGS. 17A-17C show calculated two-dimensional (2D) mode profiles on a logarithmic scale for the superimposed germanium waveguide/silicon pedestal structure with pedestal upper base widths of $d_1$=0 μm (FIG. 17A), $d_1$=0.5 μm (FIG. 17B), and $d_1$=2.5 μm (FIG. 17C).

FIGS. 17A, 17B, and 17C depict the calculated 2D mode profiles of rectangular germanium waveguides on silicon pedestals with upper base widths of 0 μm, 0.5 μm, and 2.5 μm, respectively, on a logarithmic scale (darker shading indicates higher intensity). Each plot also shows an outline of the corresponding germanium waveguide/silicon pedestal structure superimposed onto the mode profiles. FIG. 17A shows that, at a pedestal upper base width of 0 μm, the effective index is low because the evanescent wave expands into the surrounding air, which has an index of 1. As the pedestal width increases, the area of the germanium waveguide's outer surface exposed to air decreases and the contact between the waveguide and silicon increases, causing the effective index to increase. For a pedestal width of 2.5 μm (equal to the waveguide width), the mode expands into the silicon pedestal, resulting in the loss of confinement shown in FIG. 17C.

In a mid-IR germanium waveguide, the loss of the mode into air is balanced with the loss of the mode into the silicon pedestal. Because silicon absorbs at IR wavelengths above about 6.5 μm, reducing the pedestal upper base width may improve the germanium waveguide's efficiency even though it results in loss of the mode into the air. A pedestal upper base width of 0.5 μm is selected for the following simulations.

Figure 18:
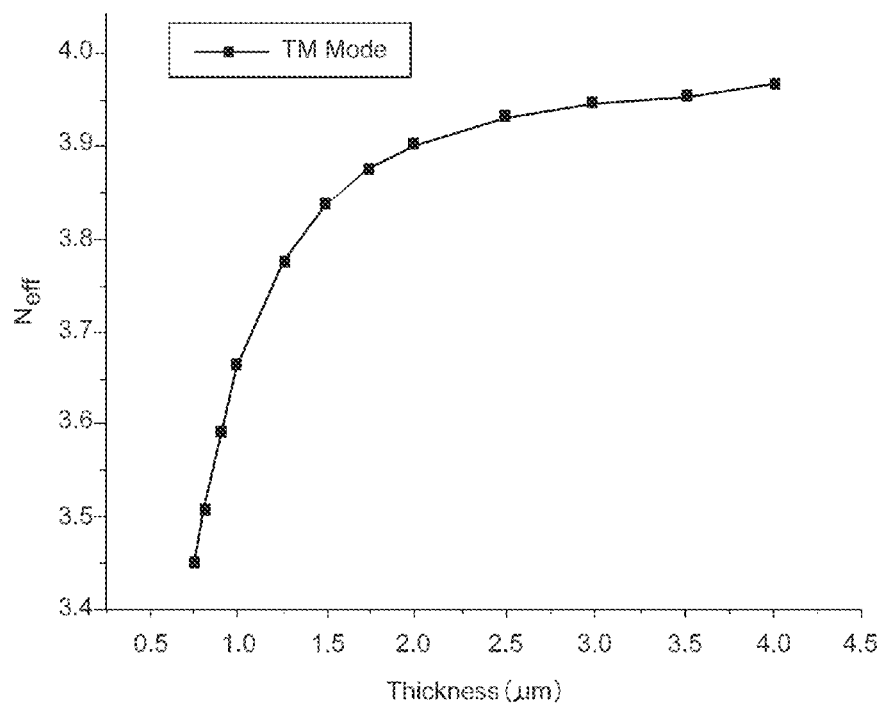
FIG. 18 is a plot of the effective mode index versus waveguide thickness for a germanium waveguide on a silicon pedestal.

FIG. 18 is a plot of the effective index for the TM mode versus waveguide height (thickness) for a rectangular germanium waveguide on an isoceles trapezoidal silicon pedestal with an upper base width of 0.5 µm and a base angle of about 54.7°. The waveguide width is kept at a constant w=2.5 µm, and the wavelength is set to 2=3.4 µm. The waveguide thickness is varied from h=0.75 µm to h=4.0 µm in increments of 0.05 µm from h=0.75 µm to h=0.8 µm, increments of 0.1 µm from h=0.8 µm to h=1.0 µm, increments of 0.25 µm from h=1.0 µm to h=2.5 µm, and increments of 0.5 µm from h=2.5 µm to h=4.0 µm. FIG. 18 shows that the effective index increases with the waveguide thickness, which is consistent with the fact that a thicker waveguide contains more material in the vertical direction and can better confine the mode. It also shows that the effective mode index plateaus at waveguide thicknesses (heights) above about h=2.0 µm.

Figures 19A, 19B, 19C:
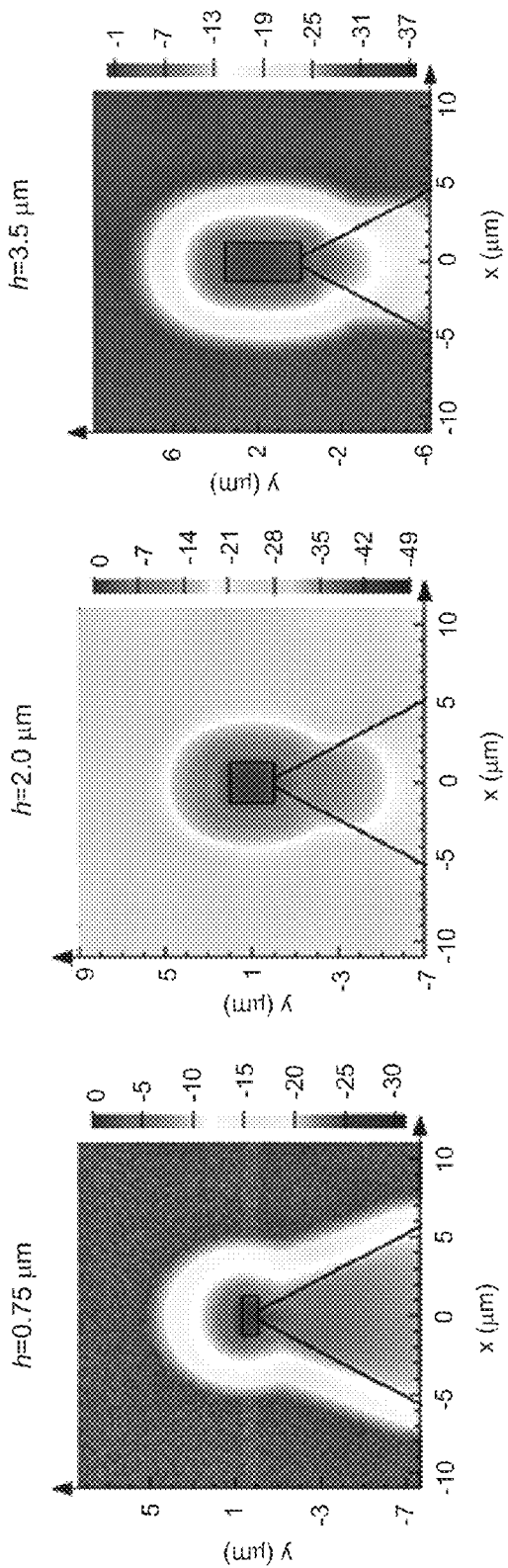
FIGS. 19A-19C show calculated 2D mode profiles on a logarithmic scale for the superimposed germanium waveguide/silicon pedestal structure with a waveguide widths of 0.75 μm (FIG. 19A), 2.0 μm (FIG. 19B), and 3.5 μm (FIG. 19C).

FIGS. 19A, 19B, and 19C depict the calculated 2D mode profiles of rectangular germanium waveguides on silicon pedestal with waveguide widths of 0.75 µm, 2.0 µm, and 3.5 µm, respectively, on a logarithmic scale (darker shading indicates higher intensity. Each plot also shows an outline of the corresponding germanium waveguide/silicon pedestal structure superimposed onto the mode profiles. The waveguide's width is w=2.5 µm and the pedestal's upper base width is $d_1$=0.5 µm. In the 3.5 µm thick waveguide (FIG. 19C), less of the mode leaks into the silicon pedestal, whereas in the 0.75 µm thick waveguide (FIG. 19A), the mode is supported by both the germanium waveguide and the silicon pedestal. Put differently, a thicker waveguide tends to confine the mode better than a thinner waveguide.

Figures 20A, 20B:
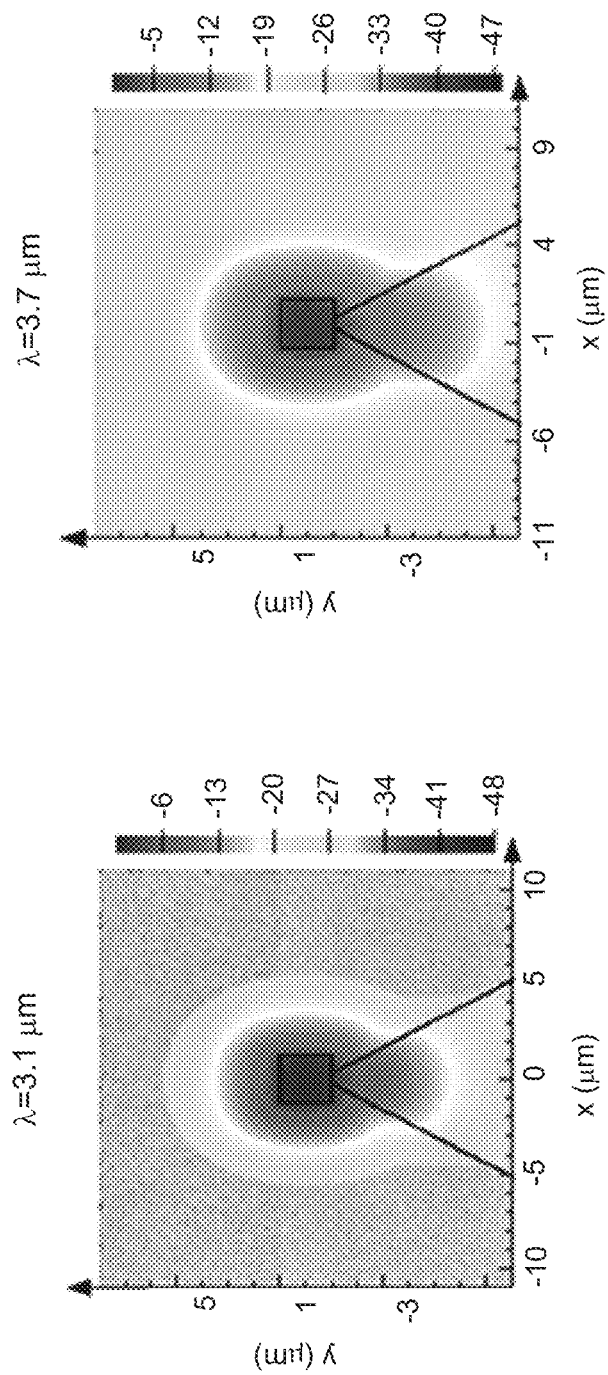
FIGS. 20A and 20B show calculated 2D mode profiles on a logarithmic scale for the superimposed germanium waveguide/silicon pedestal structure at wavelengths of 3.1 μm and 3.7 μm, respectively.
Figure 20C:
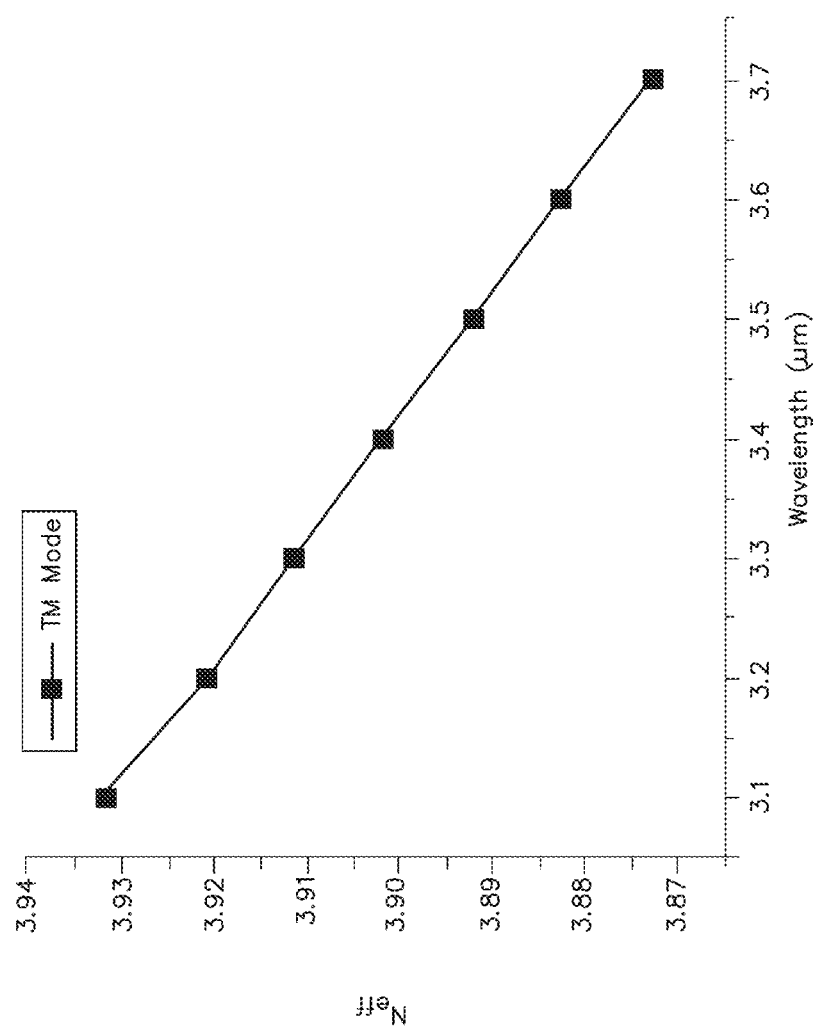
FIG. 20C is a plot of the effective mode index versus wavelength for the germanium waveguide/silicon pedestal structure shown in FIGS. 20A and 20B.

FIGS. 20A and 20B are calculated log-scale mode profiles of beams at wavelengths of λ=3.1 µm and 2=3.7 µm, respectively, for a rectangular germanium waveguide on a silicon pedestal. Darker shading indicates higher intensity. The waveguide width is w=2.5 µm, the waveguide height (thickness) is h=2.0 µm, and the pedestal upper base width is $d_1$=0.5 µm. FIG. 20C is a plot of the effective mode index at wavelengths from 2=3.1 µm to 2=3.7 µm in increments of 0.1 µm. As expected, FIGS. 20A-20C show that the effective index of the mode and mode confinement decreases with increasing wavelength.

Figure 21A:
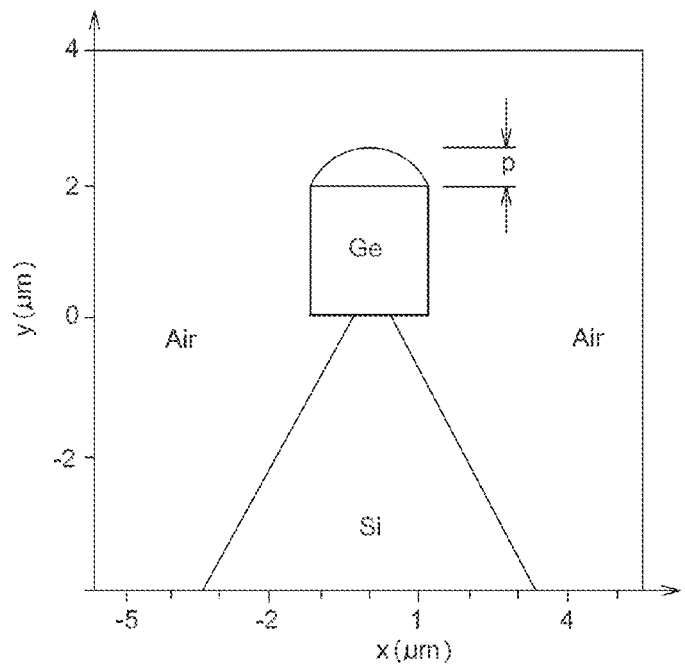
FIG. 21A shows the refractive index profile of a protruded germanium waveguide with a variable protrusion height p on a silicon pedestal
Figure 23A:
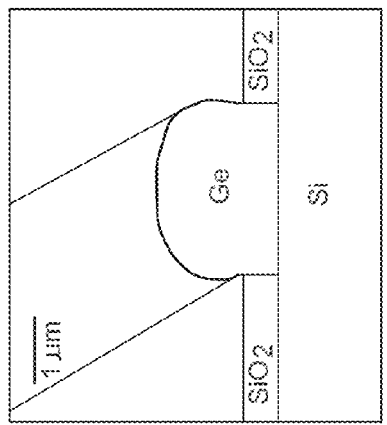
FIGS. 23A-23C are cross-sectional SEM pictures of germanium waveguides on silicon substrates at various steps in fabrication process shown in FIG. 22: after germanium deposition (FIG. 23A), after oxide removal (FIG. 23B), and in the final waveguide configuration (FIG. 23C).
Figure 23B:
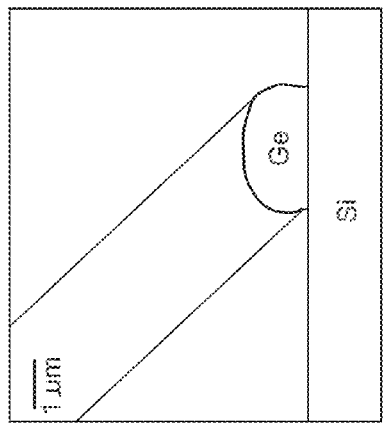
Figure 23C:
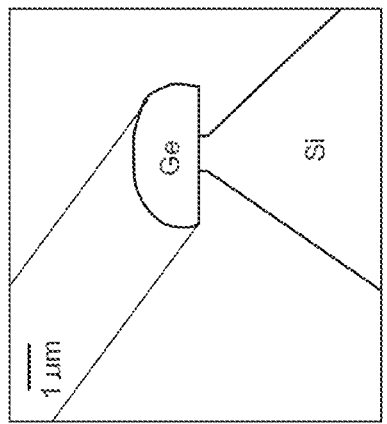

FIG. 21A is a plot of the refractive index profile of a germanium waveguide on an isosceles trapezoidal silicon pedestal, which has an upper base width of $d_1$=0.5 µm. The germanium waveguide has a width of w=2.5 µm and a sidewall height of h=2.0 µm. It is also topped by a semi-cylindrical bulge whose radius of curvature, or protrusion height p, is varied to account for fabrication imperfections (e.g., as shown in FIGS. 23A-23C).

Figure 21B:
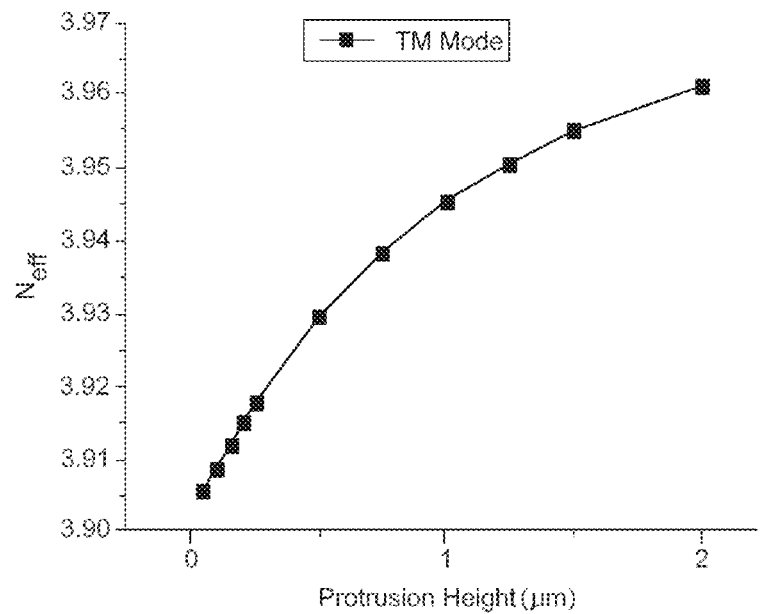
FIG. 21B is a plot of effective mode index versus protrusion height for the germanium pedestal/silicon waveguide structure of FIG. 21A.
Figure 21D:
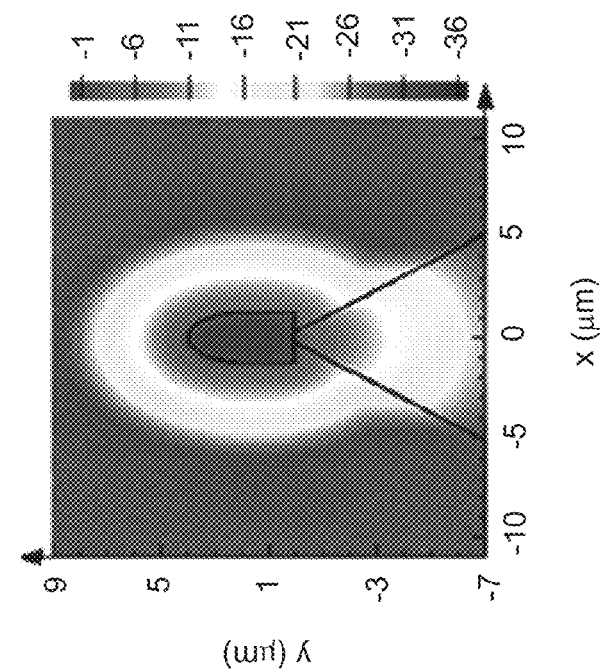
FIGS. 21C and 21D show calculated 2D mode profiles on a logarithmic scale for the superimposed germanium pedestal/silicon waveguide structures with protrusion heights p of 0.25 μm and 2.0 μm, respectively.
Figure 21C:
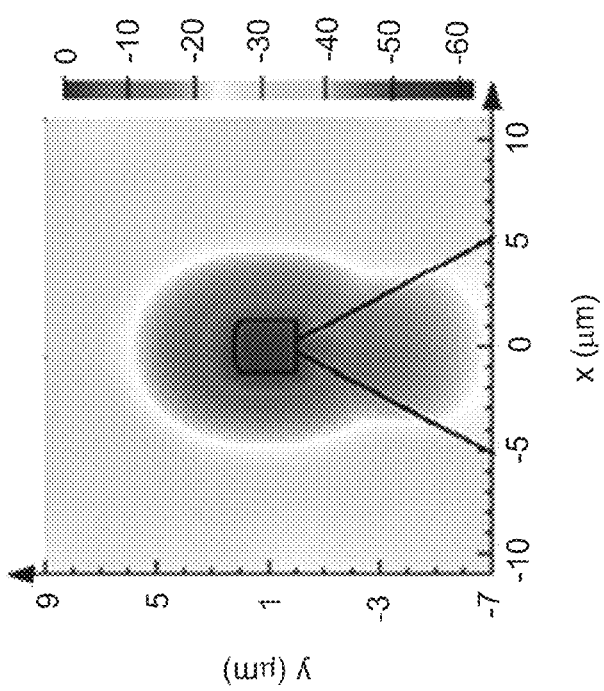
Figure 22:
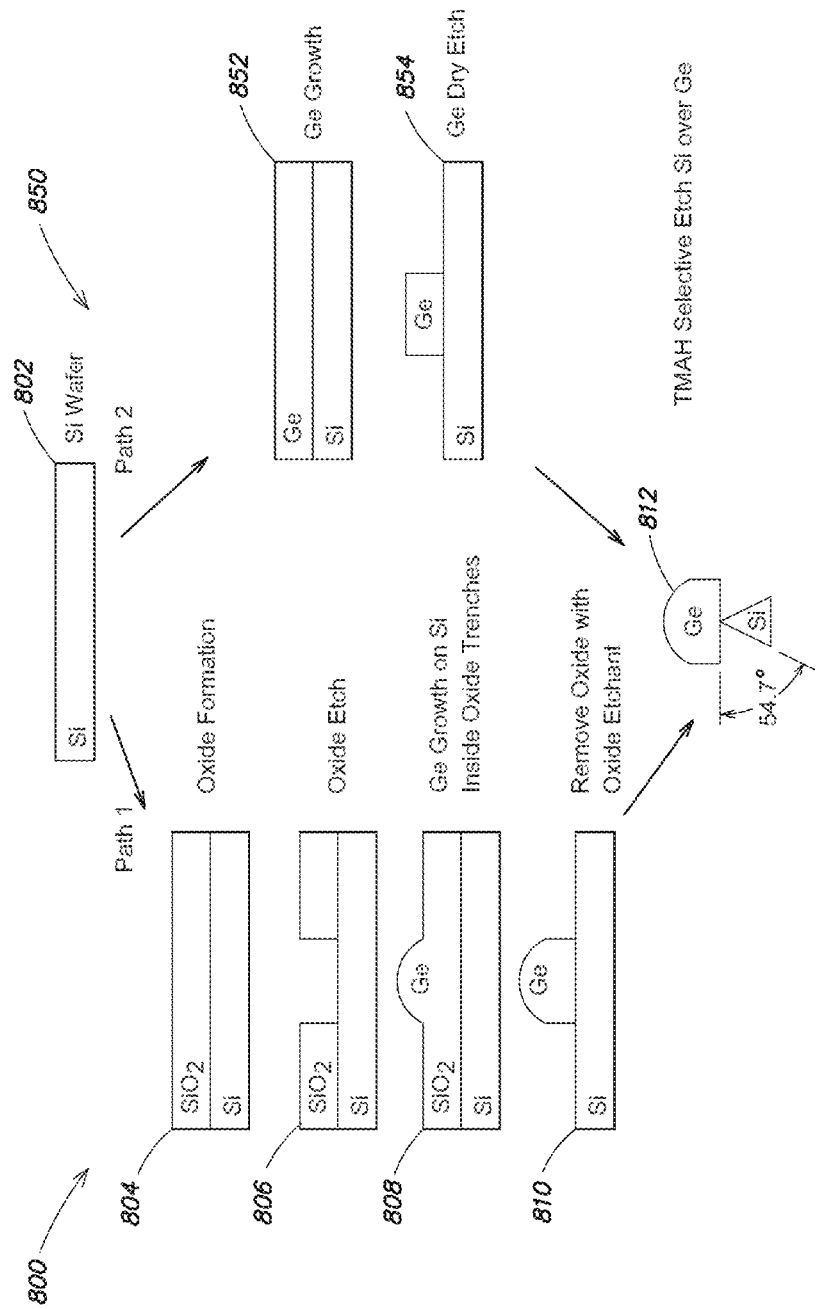
FIG. 22 shows process flows for making Ge-on-Si undercut waveguides by growing Ge waveguides selectively inside oxide trenches (left) and dry etching the as-grown Ge blanket film to form Ge waveguides (right).

FIG. 21B is a plot of the effective mode index profile for the protruded germanium waveguide/silicon pedestal structure shown in FIG. 21A at a wavelength of 2=3.4 µm for protrusion heights ranging from p=0 µm to p=2 µm. And FIGS. 21C and 21D show the mode profiles on a logarithmic scale for protrusion heights of 0.25 µm and 2.0 µm, respectively, with darker shading indicating higher intensity. (The corresponding protruded germanium waveguide/silicon pedestal structures are superimposed onto the mode profiles.) FIGS. 21B-21D shows that increasing the protrusion height increases the mode confinement and changes the mode's shape, which has implications for coupling light into and out of the waveguide.

Fabricating a Germanium Pedestal Waveguide

FIGS. 22 and 23A-23C illustrate two processes for fabricating a germanium waveguide on a silicon pedestal: a first process 800 that involves selectively growing germanium in an oxide trench and a second process 850 that involves dry etching a germanium layer on a silicon substrate. Both processes 800 and 850 start with a blanket silicon wafer (step 802). In the first process, silicon oxide is thermally grown or deposited on Si substrate (step 804). Then the silicon oxide is patterned by lithography or any other suitable process to define a trench that extends to the surface of the silicon substrate (step 806). The trench defines the shape of the germanium waveguide and can be made using a combination of dry etching and wet etching to prevent damage to the surface of the silicon substrate.

In step 808, single crystalline germanium is grown epitaxially on the exposed silicon inside the silicon oxide trench by chemical vapor deposition (CVD), such as ultra-high-vacuum CVD or reduced pressure CVD, or any other suitable germanium deposition technique. FIG. 23A is an annotated SEM image that shows the cross section of germanium waveguide grown on a silicon substrate within a trench formed in a layer of silicon dioxide on the silicon substrate's surface. In some cases, the germanium is intrinsic (undoped) to reduce free carrier absorption. Because the silicon oxide is not transparent in the mid-IR range, it is removed by wet etching with a chemical, such as a buffered oxide etchant, that selectively etches silicon oxide over germanium and silicon (step 810). FIG. 23B is an annotated SEM image that shows the cross section of germanium waveguide on a silicon substrate after removal of the silicon dioxide.

In step 812, a portion of the silicon under the germanium is selectively etched away to form a Ge-on-Si undercut waveguide. Suitable etchants include, but are not limited to tetramethylammonium hydroxide (TMAH) solution and potassium hydroxide (KOH), each of which wet etches silicon but not germanium. Anisotropic etching of the silicon (100) planes and (111) planes causes sidewalls of the silicon pedestal to form an angle of about 54.7° with the bottom of the germanium waveguide. The anisotropic etching in step 812 can be carried out with solution temperatures ranging from room temperature (about 25° C.) to about 90° C. and at solution concentrations selected based on the desired etching rates of the silicon (100) and (111) planes. For example, putting the germanium waveguide/silicon substrate shown in FIG. 23B into a 25% TMAH solution at 70° C. for 150 minutes yield the germanium waveguide/silicon pedestal shown in FIG. 23C. FIG. 23C shows that the angle between the pedestal sidewall and the bottom of the waveguide is about 54.7°, the pedestal upper base width $d_1$ is about 500 nm, and the waveguide width w is about 2.2 µm.

In the second process 850, a germanium layer is grown epitaxially on the silicon substrate using CVD or any other suitable deposition technique in step 852. The germanium layer is patterned lithographically and dry etched down to the surface of the silicon substrate to form a germanium waveguide in step 854. The germanium waveguide is then undercut in step 812 (described above) to form a silicon pedestal underneath the germanium waveguide. Although the second process 850 has fewer steps that the first process 800, it includes dry etching that may result in a germanium waveguide with rougher sidewalls. It may also be difficult to find dry etching chemicals that etch germanium without etching silicon (much).

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of designing and making the coupling structures and diffractive optical elements disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes (e.g., of designing and making the coupling structures and diffractive optical elements disclosed above) outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method of sensing at least one molecule, the method comprising:
    guiding a mid-infrared beam having at least one spectral component in a range of about 1.5 µm to about 12.0 µm from a first end of a semiconductor waveguide, disposed on a pedestal made of crystalline silicon extending from a silicon substrate, to a second end of the semiconductor waveguide;
    exposing an outer surface of the semiconductor waveguide to the at least one molecule so as to reduce an intensity of the at least one spectral component via absorption by the at least one molecule; and
    detecting the intensity of the at least one spectral component at the second end of the semiconductor waveguide.

2. The method of claim 1, wherein guiding the mid-infrared beam comprises confining only a first portion of the mid-infrared beam within the semiconductor waveguide.

3. The method of claim 1, wherein the semiconductor waveguide comprises silicon.

4. The method of claim 1, wherein exposing the outer surface of the semiconductor waveguide to the at least one molecule includes disposing a fluid containing the at least one molecule on the outer surface of the semiconductor waveguide.

5. The method of claim 1, wherein detecting the intensity of the at least one spectral component comprises detecting a spectrum of the mid-infrared beam.

6. The method of claim 5, further comprising:
    identifying the at least one molecule based on the spectrum of the mid-infrared beam.

7. The method of claim 1, further comprising:
    generating the mid-infrared beam; and
    coupling the mid-infrared beam into the semiconductor waveguide via the first end of the semiconductor waveguide.

8. The method of claim 7, wherein generating the mid-infrared beam comprises emitting radiation having a bandwidth of about 1.0 µm to about 12.0 µm.

9. The method of claim 1, further comprising:
    tuning a wavelength of the at least one spectral component; and
    detecting a change in the intensity of the at least one spectral component as a function of time; and
    determining an absorption spectrum of the at least one molecule based on the change in the intensity.

10. A method of sensing at least one molecule, the method comprising:
    guiding a mid-infrared beam having at least one spectral component in a range of about 1.5 µm to about 12.0 µm from a first end of a semiconductor waveguide, disposed on a silicon pedestal extending from a silicon substrate, to a second end of the silicon waveguide;
    exposing an outer surface of the semiconductor waveguide to the at least one molecule so as to reduce an intensity of the at least one spectral component via absorption by the at least one molecule; and
    detecting the intensity of the at least one spectral component at the second end of the semiconductor waveguide,
    wherein the semiconductor waveguide comprises germanium.

11. A device for sensing at least one molecule with a mid-infrared beam having at least one spectral component at a wavelength of about 1.5 µm to about 12.0 µm, the device comprising:
    a silicon substrate;
    a pedestal made of crystalline silicon extending from the silicon substrate; and
    a semiconductor waveguide, disposed on the pedestal above the silicon substrate, to guide the mid-infrared beam, the semiconductor waveguide defining an outer surface to receive the at least one molecule so as to cause absorption of the at least one spectral component by the at least one molecule.

12. The device of claim 11, wherein the semiconductor waveguide comprises silicon.

13. The device of claim 11, further comprising:
    a mid-infrared light source, optically coupled to a first end of the semiconductor waveguide, to launch the mid-infrared beam into the semiconductor waveguide; and
    a detector, optically coupled to a second end of the semiconductor waveguide, to detect the mid-infrared beam transmitted through the semiconductor waveguide and to provide a signal representative of the absorption of the at least one spectral component.

14. The device of claim 13, wherein at least one of the light source and the detector is disposed on the substrate.

15. The device of claim 13, wherein the light source is configured to tune a wavelength of the at least one spectral component of the mid-infrared beam.

16. The device of claim 13, wherein the light source is configured to emit mid-infrared radiation having a bandwidth of about 1 μm to about 6.5 μm.

17. The device of claim 13, wherein the detector is configured to detect a spectrum of the mid-infrared beam transmitted through the semiconductor waveguide.

18. A device for sensing at least one molecule with a mid-infrared beam having at least one spectral component at a wavelength of about 1.5 μm to about 12.0 μm, the device comprising:
    a silicon substrate;
    a silicon pedestal extending from the silicon substrate; and
    a semiconductor waveguide, disposed on the silicon pedestal above the silicon substrate, to guide the mid-infrared beam, the semiconductor waveguide defining an outer surface to receive the at least one molecule so as to cause absorption of the at least one spectral component by the at least one molecule,
    wherein the silicon pedestal has a minimum width of about 0.5 μm to about 2.5 μm and a height of about 1.0 μm to about 20 μm.

19. A device for sensing at least one molecule with a mid-infrared beam having at least one spectral component at a wavelength of about 1.5 μm to about 12.0 μm, the device comprising:
    a silicon substrate;
    a silicon pedestal extending from the silicon substrate; and
    a semiconductor waveguide, disposed on the silicon pedestal above the silicon substrate, to guide the mid-infrared beam, the semiconductor waveguide defining an outer surface to receive the at least one molecule so as to cause absorption of the at least one spectral component by the at least one molecule,
    wherein the semiconductor waveguide has a width of about 1 μm to about 30 μm and a height of about 0.4 μm to about 50 μm.

20. A device for sensing at least one molecule with a mid-infrared beam having at least one spectral component at a wavelength of about 1.5 μm to about 12.0 μm, the device comprising:
    a silicon substrate;
    a silicon pedestal extending from the silicon substrate; and
    a semiconductor waveguide, disposed on the silicon pedestal above the silicon substrate, to guide the mid-infrared beam, the semiconductor waveguide defining an outer surface to receive the at least one molecule so as to cause absorption of the at least one spectral component by the at least one molecule,
    where the semiconductor waveguide comprises germanium.

21. A method of making a silicon waveguide on a pedestal made of crystalline silicon extending from a silicon substrate, the method comprising:
    (A) forming a silicon ridge on the silicon substrate;
    (B) disposing a conformal layer of silicon dioxide on the silicon ridge so as to form a coated silicon ridge adjacent to an exposed portion of the silicon substrate;
    (C) etching the exposed portion of the silicon substrate so as to create the pedestal made of crystalline silicon extending from the silicon substrate and supporting the coated silicon ridge; and
    (D) removing the conformal layer of silicon dioxide from the coated silicon ridge so as to form the silicon waveguide on the pedestal made of crystalline silicon.

22. The method of claim 21, wherein (A) comprises:
    (A1) depositing a silicon dioxide layer on the silicon substrate;
    (A2) patterning the silicon dioxide layer so as to form a silicon dioxide ridge on the silicon substrate; and
    (A3) etching the silicon substrate adjacent to the silicon dioxide ridge so as to form the silicon ridge beneath the silicon dioxide ridge.

23. The method of claim 22, wherein (A2) comprises at least one of reactive ion etching and wet anisotropic etching.

24. The method of claim 21, wherein (B) comprises:
    (B1) depositing a silicon dioxide layer on the silicon ridge and the silicon substrate; and
    (B2) anisotropically etching the silicon dioxide layer so as to form the exposed portion of the silicon substrate.

25. The method of claim 24, wherein (B2) comprises at least one of reactive ion etching and wet anisotropic etching.

26. A method of making a silicon waveguide on a silicon pedestal extending from a silicon substrate, the method comprising:
    (A) forming a silicon ridge on the silicon substrate;
    (B) disposing a conformal layer of silicon dioxide on the silicon ridge so as to form a coated silicon ridge adjacent to an exposed portion of the silicon substrate;
    (C) etching the exposed portion of the silicon substrate so as to create the silicon pedestal extending from the silicon substrate and supporting the coated silicon ridge; and
    (D) removing the conformal layer of silicon dioxide from the coated silicon ridge so as to form the silicon waveguide on the silicon pedestal,
    wherein (A) comprises selecting a width of the silicon ridge to be about 1 μm to about 30 μm and a height of the silicon ridge to be about 1 μm to about 30 μm.

27. A method of making a silicon waveguide on a silicon pedestal extending from a silicon substrate, the method comprising:
    (A) forming a silicon ridge on the silicon substrate;
    (B) disposing a conformal layer of silicon dioxide on the silicon ridge so as to form a coated silicon ridge adjacent to an exposed portion of the silicon substrate;
    (C) etching the exposed portion of the silicon substrate so as to create the silicon pedestal extending from the silicon substrate and supporting the coated silicon ridge; and
    (D) removing the conformal layer of silicon dioxide from the coated silicon ridge so as to form the silicon waveguide on the silicon pedestal,
    wherein (C) comprises exposing the exposed portion of the substrate to $SF_6$.

28. A method of making a silicon waveguide on a silicon pedestal extending from a silicon substrate, the method comprising:
    (A) forming a silicon ridge on the silicon substrate;
    (B) disposing a conformal layer of silicon dioxide on the silicon ridge so as to form a coated silicon ridge adjacent to an exposed portion of the silicon substrate;

(C) etching the exposed portion of the silicon substrate so as to create the silicon pedestal extending from the silicon substrate and supporting the coated silicon ridge; and (D) removing the conformal layer of silicon dioxide from the coated silicon ridge so as to form the silicon waveguide on the silicon pedestal, wherein (C) comprises isotropically etching the exposed portion of the silicon substrate to a depth of about 1 μm to about 20 μm so as to form the silicon pedestal with a height of about 1 μm to about 20 μm.

29. A method of making a silicon waveguide on a silicon pedestal extending from a silicon substrate, the method comprising:

(A) forming a silicon ridge on the silicon substrate;

(B) disposing a conformal layer of silicon dioxide on the silicon ridge so as to form a coated silicon ridge adjacent to an exposed portion of the silicon substrate;

(C) etching the exposed portion of the silicon substrate so as to create the silicon pedestal extending from the silicon substrate and supporting the coated silicon ridge; and (D) removing the conformal layer of silicon dioxide from the coated silicon ridge so as to form the silicon waveguide on the silicon pedestal, wherein (C) comprises etching the exposed portion of the silicon substrate so as to form the silicon pedestal with a width of about 0.5 μm to about 2.5 μm.

30. A method of making a germanium waveguide on a silicon pedestal extending from a silicon substrate, the method comprising:

(A) forming a germanium waveguide on the silicon substrate; and (B) anisotropically etching at least a portion of the silicon substrate so as to create a silicon pedestal extending from the silicon substrate and supporting the germanium waveguide.

31. The method of claim 30, wherein (A) comprises:

(A1) forming an oxide layer on the silicon substrate;

(A2) selectively etching the oxide layer to form a trench that extends to the silicon substrate;

(A3) depositing germanium in the trench; and (A4) removing the oxide layer to form the germanium waveguide.

32. The method of claim 30, wherein (A) comprises:

(A1) forming a germanium layer on the silicon substrate;

(A2) selectively etching the germanium layer to form the germanium waveguide.

* * * * *

UNITED STATES PATENT AND TRADEMARK OFFICE
CERTIFICATE OF CORRECTION

| | | |
|---|---|---|
| PATENT NO. | : 9,046,650 B2 | Page 1 of 1 |
| APPLICATION NO. | : 14/076655 | |
| DATED | : June 2, 2015 | |
| INVENTOR(S) | : Pao Tai Lin et al. | |

It is certified that error appears in the above-identified patent and that said Letters Patent is hereby corrected as shown below:

In the Specification,

In Column 1, Lines 15-17: please replace

'This invention was made with government support under Contract no. DE-NA000421 from the Department of Energy. The government has certain rights in the invention.' with

--This invention was made with government support under Contract No. DE-NA0000421 awarded by the Department of Energy. The government has certain rights in the invention.--

Signed and Sealed this
Twenty-second Day of September, 2015

Michelle K. Lee
*Director of the United States Patent and Trademark Office*